(12) United States Patent
Somani et al.

(10) Patent No.: US 11,535,872 B2
(45) Date of Patent: Dec. 27, 2022

(54) MICROBIAL STRAINS AND USES THEREOF

(71) Applicant: Aberystwyth University, Aberystwyth (GB)

(72) Inventors: Abhishek Somani, Aberystwyth (GB); David Neil Bryant, Aberystwyth (GB); Sreenivas Rao Ravella, Aberystwyth (GB); Joseph Anthony Gallagher, Aberystwyth (GB); Narcis Fernandez-Fuentes, Aberystwyth (GB)

(73) Assignee: Aberystwyth University, Aberystwyth (GB)

( * ) Notice: Subject to any disclaimer, the term of this patent is extended or adjusted under 35 U.S.C. 154(b) by 119 days.

(21) Appl. No.: 16/641,318

(22) PCT Filed: Aug. 24, 2018

(86) PCT No.: PCT/GB2018/052416
§ 371 (c)(1),
(2) Date: Feb. 24, 2020

(87) PCT Pub. No.: WO2019/038565
PCT Pub. Date: Feb. 28, 2019

(65) Prior Publication Data
US 2020/0385764 A1 Dec. 10, 2020

(30) Foreign Application Priority Data
Aug. 24, 2017 (GB) .................................... 1713622

(51) Int. Cl.
| | | |
|---|---|---|
| *C12N 1/18* | (2006.01) | |
| *C12N 1/22* | (2006.01) | |
| *C12P 7/18* | (2006.01) | |
| *C12N 1/16* | (2006.01) | |
| *C12R 1/72* | (2006.01) | |
| *C12R 1/74* | (2006.01) | |

(52) U.S. Cl.
CPC ................ *C12P 7/18* (2013.01); *C12N 1/165* (2021.05); *C12N 1/18* (2013.01); *C12N 1/22* (2013.01); *C12R 2001/72* (2021.05); *C12R 2001/74* (2021.05)

(58) Field of Classification Search
CPC . C12R 2001/72; C12R 2001/74; C12N 1/165; C12N 1/22; C12N 1/18; C12P 7/18
See application file for complete search history.

(56) References Cited

U.S. PATENT DOCUMENTS

2008/0206821 A1* 8/2008 Kim et al. ...................... 435/72

FOREIGN PATENT DOCUMENTS

| CN | 105062908 | | 11/2015 | |
|---|---|---|---|---|
| EP | 0950712 | A1 * | 10/1999 | ............. C12N 15/68 |
| EP | 2519626 | A1 | 11/2012 | |
| WO | WO 2017/037745 | A1 | 3/2017 | |
| WO | WO-2018/112639 | | 6/2018 | |

OTHER PUBLICATIONS

Coelho et al., Extensive Intra-Kingdom Horizontal Gene Transfer Converging on a Fungal Fructose Transporter Gene, PLoS Genetics, vol. 9(6): el003587, Jun. 2013.
Gorsich et al., Tolerance to furfural-induced stress is associated with pentose phosphate pathway genes ZWF 1, GND 1, RPE1, and TKL1 in *Saccharomyces cerevisiae*, Applied Microbiology and Biotechnology, vol. 71(3):339-349, Jul. 2006.
Jeon et al., Xylitol production from a mutant strain of Candida tropicalis, Letters in Applied Microbiology, vol. 53(1):106-13, Jul. 2011.
Jönsson et al., N.-O., 2013. Bioconversion oflignocellulose: inhibitors and detoxification, Biotechnology for Biofuels, vol. 6(1):16, 2013.
Ko et al., Production of xylitol from D-xylose by a xylitol dehydrogenase gene-disrupted mutant of Candida tropicalis, Applied and Environmental Microbiology, vol. 72(6):4207-4213, Jun. 2006.
Koppram, et al., The presence of pretreated lignocellulosic solids from birch during *Saccharomyces cerevisiae* fermentations leads to increased tolerance to inhibitors—A proteomic study of the effects, PLoS ONE, vol. 11(2):e0148635, Feb. 2016.
Lages, F. & Lucas, C., Contribution to the physiological characterization of glycerol active uptake in *Saccharomyces cerevisiae*, Biochimica et Biophysica Acta (EBA)—Bioenergetics, vol. 1322(1):8-18, Nov. 1997.
Porman et al., MTL-Independent Phenotypic Switching in Candida tropicalis and a Dual Role for Worll in Regulating Switching and Filamentation, PLoS Genetics, vol. 9(3):e1003369, Mar. 2013.
Seervai et al., Parasexuality and ploidy change in Candida tropicalis, Eukmyotic Cell, vol. 12(12):1629-1640, Dec. 2013.
Young et al., Optimizing pentose utilization in yeast: the need for novel tools and approaches, Biotechnology for Biofuels, vol. 3(512):24, Nov. 2010.
Qi et al., Biosynthesis of Xylitol from Glucose: Microorganisms, Key Enzymes and Genetically Engineered Strains, American Journal of Bioscience and Bioengineering, vol. 5(5):109-112, Oct. 2017.
Somani et al., Draft Genome Assemblies of Xylose-Utilizing Candida tropicalis and Candida boidinii with Potential Application in Biochemical and Biofuel Production, vol. 6(7):e01594-17, Feb. 2018.
Navnit et al., Isolation and Screening of Wild Yeast for Maximum Xylitol Production, International Journal of Life Sciences, vol. A5:11-18, Dec. 2015.
Baraththkannan et al., Optimization of Parameters to Increase the Xylose Reductase Production from Candida Tropicalis Strain LY15 Using Corn Cob as Hemicellulose Waste Substrates, African Journal of Microbiology Research, vol. 10(45):1908-1915, Dec. 2016.
International Search Report and Written Opinion dated Oct. 25, 2018 issued in International Patent Application No. PCT/GB2018/052416.

(Continued)

*Primary Examiner* — Satyendra K Singh
(74) *Attorney, Agent, or Firm* — Howson & Howson LLP

(57) ABSTRACT

The present invention relates to *Candida* strains comprising a mutation or deletion in the first and/or second XYL2 allele which can be used for producing one or more sugar alcohols from a lignocellulosic feedstock. The preferred sugar alcohol is xylitol.

16 Claims, 24 Drawing Sheets

Specification includes a Sequence Listing.

(56) References Cited

OTHER PUBLICATIONS

Meinander et al., Fermentation of xylose/glucose mixtures by metabolically engineered *Saccharomyces cerevisiae* strains expressing XYL1 and XYL2 from Pichia stipites with and without overexpression of TAL1, Bioresource Technology, vol. 81(1):79-87, Apr. 199.
Pienkos et al., Role of pretreatment and conditioning processes on toxicity of lignocellulosic biomass hydrolysates, Cellulose, vol. 16(4):743-762, Jun. 2009.
Prasad et al., Ethanol as an alternative fuel from agricultural, industrial and urban residues, Resources, Conservation and Recycling, vol. 50(1):1-39, Mar. 2007.
Sato et al., The effects of oral xylitol administration on bone density in rat femur, Odontology, vol. 99(1):28-33, Jan. 2011.
Tamburini et al., Cosubstrate effect on xylose reductase and xylitol dehydrogenase activity levels, and its consequence on xylitol production by Candida tropicalis, Enzyme and Microbial Technology, vol. 46(5), pp. 352-359, Apr. 2010.
Yoon et al., L-Arabinose Pathway Engineering for Arabitol-Free Xylitol Production in Candida Tropicalis, Biotechnology Letters, vol. 33(4):747-53, Apr. 2011.
Abreu et al., Mixotrophic cultivation of Chlorella vulgaris using industrial dairy waste as organic carbon source, Bioresource Technology, vol. 118:61-6, Aug. 2012.
Ahmad et al., Enhancement of xylitol production in Candida tropicalis by coexpression of two genes involved in pentose phosphate pathway, Bioprocess and Biosystems Engineering, vol. 3 5(1-2):199-204, Jan. 2012.
Ahmad et al., Enhancement of xylitol production in glycerol kinase disrupted Candida tropicalis by co-expression of three genes involved in glycerol metabolic pathway, Bioprocess and Biosystems Engineering, vol. 36(9):1279-84, Dec. 2012.
Ko et al., Enhancement of xylitol production by attenuation of intracellular xylitol dehydrogenase activity in Candida tropicalis, Biotechnology Letters, vol. 33(6):1209-1213, Jun. 2011.
Makinen et al., Six-month polyol chewing-gum programme in kindergarten-age children: a feasibility study focusing on mutans streptococci and dental plaque, International Dental Journal, vol. 55(2):81-88, Apr. 2005.
Park et al., Recent advances in biological production of sugar alcohols, Current Opinion in Biotechnology, vol. 37:105-113, Feb. 2016.
Ravella et al., *Candida northwykensis* sp. Nov., A Novel Yeast Isolated from the Gut of the Click Beetle Melanotus villosus, Current Microbiology, vol. 63(2):115-120, Aug. 2011.
Reuss et al., The SAT1 flipper, an optimized tool for gene disruption in Candida albicans, Gene, vol. 341:119-27, Oct. 2004.
Sahin et al., Sugar reduction in bakery products: Current strategies and sourdough technology as a potential novel approach, Food Research International, vol. 126:108583, Dec. 2019.
Uhari et al., A Novel Use of Xylitol Sugar in Preventing Acute Otitis Media, Pediatrics, vol. 102(4):879-884, Oct. 1998.
Wang et al., Effect of Selected Aldehydes found in the Corncob Hemicellulose Hydrolysate on the Growth and Xylitol Fermentation of Candida tropicalis, Biotechnology Progress, vol. 29(5):1181-9, Sep. 2013.
Wang et al., Metabolic responses in Candida tropicalis to complex inhibitors during xylitol bioconversion, Fungal Genetics and Biology, vol. 82:1-8, Sep. 2015.
Ping, Y et al., "Xylitol production form non-detoxified corncob hemicellulose acid hydrolystate by Candida tropicalis," Biochemical Engineering Journal, vol. 75, Jun. 2013, pp. 86-91.
Mattam, AJ. et al., "Cellulolytic enzyme expression and simultaneous conversion of lignocellulosic sugars into ethanol and xylitol by a new Candida tropicalis strain," Biotechnology for biofuels, vol. 9, Jul. 2016, p. 157.
Matos, ITSR, et al., "Isolation and Characterization of Yeasts Able to Assimilate Sugarcane Bagasse Hemicellulosic Hydrolysate and Produce Xylitol Associated with Veturius transversus (Passalidae, Coleoptera, and Insecta)," International Journal of Microbiology, vol. 2017, Article ID 5346741, 6 pages, 2017. https://doi.org/10.1155/2017/5346741.
Rao, RS et al., "Isolation and characterization of xylitol-producing yeasts from the gut of colleopteran insects," Curr Microbiol., vol. 55, No. 5, Dec. 2007, pp. 441-446.
Jamai, L et al., "Production of ethanol from starch by free and immobilized Candida tropicalis in the presence of alpha-amylase," Bioresource Technology, vol. 98, No. 13, Oct. 2007, pp. 2765-2770.
Suksham, Pal et al., "Molecular strategies for enhancing microbial production of xylitol," Process Biotechnology vol. 51, Jul. 2016, pp. 809-819. (XP029561687).
Search Report issued on UK Patent Application No. GB 1713622.7, dated Oct. 9, 2017.
Examination Report for Indian Patent Application No. 20217011451, dated Nov. 17, 2021.

* cited by examiner

G

SEQUENCE LISTING

```
<160> NUMBER OF SEQ ID NOS: 20

<210> SEQ ID NO 1
<211> LENGTH: 34
<212> TYPE: DNA
<213> ORGANISM: Artificial Sequence
<220> FEATURE:
<223> OTHER INFORMATION: Primer Xyl2 -500

<400> SEQUENCE: 1
ggtggtggta cctgttttgg aattcaattt tccc                              34

<210> SEQ ID NO 2
<211> LENGTH: 39
<212> TYPE: DNA
<213> ORGANISM: Artificial Sequence
<220> FEATURE:
<223> OTHER INFORMATION: Primer Xyl2 0

<400> SEQUENCE: 2
ggtggtctcg agtgactttt gtatttgtag aattgaaag                         39

<210> SEQ ID NO 3
<211> LENGTH: 48
<212> TYPE: DNA
<213> ORGANISM: Artificial Sequence
<220> FEATURE:
<223> OTHER INFORMATION: Primer Xyl2 +1095

<400> SEQUENCE: 3
ggtggtgagc tcaggtatat agtattagaa aaagaatata cagtatat               48
```

<210> SEQ ID NO 4
<211> LENGTH: 41
<212> TYPE: DNA
<213> ORGANISM: Artificial Sequence
<220> FEATURE:
<223> OTHER INFORMATION: Primer Xyl2 +1566

<400> SEQUENCE: 4
ggtggtgcat gcaataaatc ttgtatacca aatttcttag c                41

<210> SEQ ID NO 5
<211> LENGTH: 31
<212> TYPE: DNA
<213> ORGANISM: Artificial Sequence
<220> FEATURE:
<223> OTHER INFORMATION: Primer Xyl2 +59 FP

<400> SEQUENCE: 5
cggggtaccc gaagctccaa aactcgaatc a                           31

<210> SEQ ID NO 6
<211> LENGTH: 30
<212> TYPE: DNA
<213> ORGANISM: Artificial Sequence
<220> FEATURE:
<223> OTHER INFORMATION: Primer Xyl2 +372 RP

<400> SEQUENCE: 6
tccgctcgag catctgggtt aactggtggg                             30

<210> SEQ ID NO 7
<211> LENGTH: 30
<212> TYPE: DNA
<213> ORGANISM: Artificial Sequence
<220> FEATURE:
<223> OTHER INFORMATION: Primer Xyl2 +749 FP

<400> SEQUENCE: 7
ggtgagctcg gaatgtagtg gtgctcaacc                             30

<210> SEQ ID NO 8
<211> LENGTH: 31
<212> TYPE: DNA
<213> ORGANISM: Artificial Sequence
<220> FEATURE:
<223> OTHER INFORMATION: Primer Xyl2 +1061 RP

<400> SEQUENCE: 8
acatgcatgc accatttcct gctctgacca a                           31

<210> SEQ ID NO 9
<211> LENGTH: 24
<212> TYPE: DNA
<213> ORGANISM: Artificial Sequence
<220> FEATURE:
<223> OTHER INFORMATION: Xyl2 Primer 63

<400> SEQUENCE: 9
tgaatagatt gtaggacctt ggca                                   24

<210> SEQ ID NO 10
<211> LENGTH: 21
<212> TYPE: DNA
<213> ORGANISM: Artificial Sequence
<220> FEATURE:

<223> OTHER INFORMATION: Xyl2 Primer 64

<400> SEQUENCE: 10
tccttggcct tcattcttgc t                                        21

<210> SEQ ID NO 11
<211> LENGTH: 20
<212> TYPE: DNA
<213> ORGANISM: Artificial Sequence
<220> FEATURE:
<223> OTHER INFORMATION: Primer RT-PCR Xyl2 FP1

<400> SEQUENCE: 11
aacccagatg aaccaaatcc                                          20

<210> SEQ ID NO 12
<211> LENGTH: 20
<212> TYPE: DNA
<213> ORGANISM: Artificial Sequence
<220> FEATURE:
<223> OTHER INFORMATION: Primer RT-PCR Xyl2 RP1

<400> SEQUENCE: 12
accgtggaca ccaacagtta                                          20

<210> SEQ ID NO 13
<211> LENGTH: 20
<212> TYPE: DNA
<213> ORGANISM: Artificial Sequence
<220> FEATURE:
<223> OTHER INFORMATION: Primer RT-PCR Ura3 FP1

<400> SEQUENCE: 13
tattgctcaa cgtgatatgg                                          20

<210> SEQ ID NO 14
<211> LENGTH: 20
<212> TYPE: DNA
<213> ORGANISM: Artificial Sequence
<220> FEATURE:
<223> OTHER INFORMATION: Primer RT-PCR Ura3 RP1

<400> SEQUENCE: 14
gttgacctaa agcatcacct                                          20

<210> SEQ ID NO 15
<211> LENGTH: 33
<212> TYPE: DNA
<213> ORGANISM: Artificial Sequence
<220> FEATURE:
<223> OTHER INFORMATION: Primer Y660XYL2Up-FP

<400> SEQUENCE: 15
ggtcggggta ccattattat gcggtggtgg tag                           33

<210> SEQ ID NO 16
<211> LENGTH: 33
<212> TYPE: DNA

```
<213> ORGANISM: Artificial Sequence
<220> FEATURE:
<223> OTHER INFORMATION: Primer Y660XYL2Up-RP

<400> SEQUENCE: 16
ggtggtctcg agggtgaaaa tggagggtat aac                          33

<210> SEQ ID NO 17
<211> LENGTH: 32
<212> TYPE: DNA
<213> ORGANISM: Artificial Sequence
<220> FEATURE:
<223> OTHER INFORMATION: Primer Y660XYL2Down-FP

<400> SEQUENCE: 17
ggtggtccgc ggcggtcctg agtaaacaat cg                           32

<210> SEQ ID NO 18
<211> LENGTH: 33
<212> TYPE: DNA
<213> ORGANISM: Artificial Sequence
<220> FEATURE:
<223> OTHER INFORMATION: Primer Y660XYL2Down-RP

<400> SEQUENCE: 18
ggtggtgcat gccctttttgg ctgcgaaatt ttg                         33

<210> SEQ ID NO 19
<211> LENGTH: 19
<212> TYPE: DNA
<213> ORGANISM: Artificial Sequence
<220> FEATURE:
<223> OTHER INFORMATION: Primer Y6600Xyl2deletioncheck-FP

<400> SEQUENCE: 19
catctatacc accgtcagg                                          19

<210> SEQ ID NO 20
<211> LENGTH: 23
<212> TYPE: DNA
<213> ORGANISM: Artificial Sequence
<220> FEATURE:
<223> OTHER INFORMATION: Primer Y6600Xyl2deletioncheck-RP

<400> SEQUENCE: 20
gaggactctg gaattcttat cta                                     23
```

MICROBIAL STRAINS AND USES THEREOF

CROSS-REFERENCE TO RELATED APPLICATIONS

This is a National Stage Entry under 35 U.S.C. 371 of International Patent Application No. PCT/GB2018/052416, filed Aug. 24, 2018, which claims priority to UK Patent Application No. GB1713622.7, filed Aug. 24, 2017. These applications are incorporated by reference herein.

TECHNICAL FIELD OF THE INVENTION

The present invention relates to *Candida* strains, which can be used for producing one or more sugar alcohols from a range of lignocellulosic feedstock. The strains are particularly suited for lowered arabitol and high xylitol levels when in the presence of maltose as a co-substrate.

BACKGROUND TO THE INVENTION

Lignocellulosic biomass, derived from agricultural, forestry and agro-industrial wastes, is an important avenue for technology development in light of their global abundance, widespread availability and carbon-neutral, renewable nature. Typically, linear and crystalline cellulose makes up the majority of the plant biomass followed by branched, non-crystalline heteropolymeric hemicellulose along with branched lignin. To improve the economic feasibility of the lignocellulosic biomass platform and drive its widespread commercial uptake, it is crucial to devise holistic approaches for generating value added products from most of the biomass components. With a predicted market of 1 billion US$ per annum by 2020 and comprising a 12% share within the polyol market the natural sweetener xylitol is an attractive candidate to derive value from hemicellulosic xylose.

Xylitol is a sugar alcohol of the pentitol type with wide use as an additive in the dietary food, pharmaceutical and dental industry primarily on account of its low glycemic index, efficacy in reducing tooth decay (Makinen et al. 2005), preventing acute otitis media (Uhari, M., Kontiokari, T. & Niemela 1998) and enhancing bone density (Sato et al. 2011).

Commercial xylitol production is currently achieved via xylose hydrogenation using a raney nickel catalyst. Besides being cost and energy intensive due to the need of purified xylose (as the substrate) and high temperature, such chemical treatments are environmentally unsustainable and typically require additional safeguards due to the need of high pressure hydrogen gas and a toxic catalyst (Jeon et al. 2011). As a result, a number of studies have explored biotechnological means of producing xylitol by either using naturally occurring xylose-assimilating yeasts or by engineering model species from both eukaryotic and prokaryotic domains; however, a commercial process is still elusive.

Acid-catalysed steam explosion which typically involves treatment of mild acid impregnated lignocellulose with superheated steam under pressure followed by sudden decompression, readily hydrolyses the hemicellulosic backbone due to its low molecular weight and amorphous structure. Whilst this results in release of hemicellulosic sugars (mainly pentoses and a residual hexose fraction) locked within the fibres, lignocellulose pre-treatment inevitably leads to generation of secondary by-products which when present at high concentrations can be extremely inhibitory to the microorganism's growth phenotype and overall fermentation potential. Typically, employment of acidic conditions can cause dehydration of released pentoses and hexoses to form furfurals (2-furaldehydes) and 5-hydroxymethyl-2-furaldehydes (HMF) respectively. Severe process conditions, such as increased acid concentrations or high temperature during steam explosion, can form further degradation products such as aliphatic carboxylic acids (such as acetic acid, formic acid, levulinic acid) and phenolic derivatives (vanillin, syringaldehyde, coumaric acid and ferulic acid). A number of strategies have been proposed to counteract the enhanced toxicity generated via synergism between the various inhibitory compounds within lignocellulosic hydrolysates (reviewed by Jöhnsson et al. 2013). These include vaporization, enzymatic treatments, use of reducing agents, liquid-liquid interactions and perhaps most commonly used being liquid-solid interactions which involve treatment with activated charcoal (Jonsson et al. 2013). However most of these methodologies have inherent drawbacks. Besides the addition of another process step which adversely impacts process economics and operational times, detoxification procedures almost invariably cause reductions in sugar concentrations which is bound to lower product titres and consequently process productivity.

Wheat straw is an example of a readily available agricultural feedstock within Europe and availability of more than 500 million tonnes per annum puts it amongst the topmost in the world. Wheat caters to the food requirements of more than 20% of the global population and increasing demand is likely to result in augmented future production thus ensuring a steady supply of the wheat straw feedstock. In general, hemicellulose content in wheat straw tends to be around 20-25% of its dry weight (Prasad et al. 2007) and mainly comprises of xylose, and noticeable amounts of arabinose. Lower recalcitrance of the feedstock allows the use of milder pre-treatment conditions for sugar release, particularly for hemicellulose, leading to lower amounts of inhibitors in the steam-exploded hydrolysate.

In most yeast and native fungi, including members of the *Candida* clade, the metabolism of D-xylose follows an enzymatic oxidoreductive route wherein D-xylose is first reduced to xylitol via the enzyme xylose reductase (XR) followed by xylitol's oxidation to D-xylulose by xylitol dehydrogenase (XDH). D-xylulose is further converted into xylulose-5-phosphate via the action of xylulose kinase in an ATP-dependent reaction and then enters the central cellular metabolism via the pentose phosphate pathway. Both XR and XDH require cofactors, albeit different ones, for catalysing their respective reactions. Whilst XRs from most *Candida* species either solely utilize NADPH as a cofactor or enormously favour its use over NADH, XDH is predominantly NADH-dependent. In yeast, there is usually a disparity between the intracellular levels and availability of NADPH and NADH to the xylose pathway enzymes and the consequent redox imbalance is attributed to be one of the primary reasons for xylitol production. Besides xylose, XR can also bind its epimer arabinose as a substrate subsequently converting it into arabitol, an impurity which confounds post fermentation xylitol purification.

Whilst a number of reports have focussed on the application of metabolic engineering strategies for introducing and enhancing xylose to xylitol bioconversion within model yeast, studies exploring genetic manipulation of *C. tropicalis* for enhanced xylitol production are comparatively limited. Ko et al (2006) were the first to demonstrate enhanced xylitol titres in a *C. tropicalis* mutant wherein two copies of XYL2 were disrupted to completely abolish XDH activity. Although the authors could achieve theoretically maximum yields, the deletion strain typically required high amounts of glycerol to act as a co-substrate for aiding cell maintenance and NADPH regeneration (upto 0.4 g glycerol for each g of xylose) (Ko et al. 2006), a requirement which is not only detrimental for process economics but any residual glycerol in the system is likely to confound downstream purification due to the presence of additional polyol (Ko et al. 2011). Subsequently the need for a co-substrate requirement was removed, by employing site-directed mutagenesis to reduce XDH activity by 60% thereby slowing down the carbon flow further on from XDH, albeit at the expense of conversion yields which lowered from 100% to 75% of theoretical maxima (Ko et al. 2011). In conjunction with using glycerol, recent investigations have aimed to enhance the rate of xylitol formation by improving cellular NADPH availability and consequently the flux through the pentose phosphate pathway (Ahmad et al. 2012) or substituting the endogenous *C. tropicalis* glycerol kinase gene with a cohort of glycerol metabolism genes from *S. stipitis* to increase the rate of glycerol utilisation (Ahmad et al. 2013). Whilst the use of a laboratory strain in the above-mentioned studies perhaps allowed easier microbial engineering and provided first glimpses into engineered *C. tropicalis* behaviour, albeit only in synthetic media, the lack of information regarding the strains' inhibitor tolerance and the overall scale-up of the process impedes the technology's direct commercial application.

It is an object of the present invention to identify and/or develop microbial strains and methods which are able to maximise xylose to xylitol bioconversion. It would be preferred if such strains and methods could minimise or abolish wasteful arabitol production during the fermentation process. Furthermore, it would be desirable for the strains and methods to use readily available lignocellulosic feedstocks.

SUMMARY OF THE INVENTION

In accordance with an aspect of the present invention, there is provided *Candida* strain comprising a mutation or deletion in the first and/or second XYL2 allele.

The strain preferably has a deletion of the first and/or second XYL2 allele.

The *Candida* strain may encompass a number of as claimed in either claim 1 or 2, wherein the *Candida* strain comprises a number of different strains. Preferably, the *Candida* may comprise *Candida tropicalis* NCYC 4185 or *Candida tropicalis* NCYC 4186 or *Candida tropicalis* NCYC 4190 or *Scheffersomyces (Candida) shehatae* NCYC 4187 or *Scheffersomyces (Candida) shehatae* NCYC 4188 or *Scheffersomyces (Candida) shehatae* NCYC 4189 or mutants or derivatives thereof.

In related aspects, it is preferred that the *Candida* strain is for use in producing one or more sugar alcohols from a lignocellulosic feedstock.

The *Candida* strain may be derived or isolated from the gut or larvae of a xylophagous organism.

The one or more sugar alcohols may comprise arabitol. The one or more sugar alcohols will preferably comprises xylitol.

The one or more sugar alcohols may comprise xylitol and arabitol.

Advantageously, the present inventors have found that the *Candida* strains of the present invention produce a higher xylitol to arabitol ratio than strains without a mutation or deletion in the first and/or second XYL2 allele. Strains with a mutation or deletion in the first and/or second XYL2 allele lowers arabitol levels by lowering arabinose uptake.

In embodiments of the invention, the ratio of xylitol to arabitol produced is greater than about 1.5 fold, about 2.0 fold, about 2.5 fold, about 2.7 fold, about 2.8 fold, about 2.9 fold or about 3.0 fold. In preferred embodiments, the ratio of xylitol to arabitol produced is greater than about 2.0 fold. In most preferred embodiments, the ratio of xylitol to arabitol produced is about 2.7 fold.

The ratio of xylitol to arabitol produced may be about 4:1 or more, about 5:1 or more, about 6:1 or more, about 7:1 or more, about 8:1 or more, about 7:1 or more, about 8:1 or more, about 9:1 or more, about 10:1 or more, about 11:1 or more, about 12:1 or more, about 13:1 or more, about 14:1 or more, about 15:1 or more, about 16:1 or more, about 17:1 or more, about 18:1 or more, about 19:1 or more, or about 20:1 or more. In certain embodiments of the invention, the ratio of xylitol to arabitol produced is about 4:1 or more. More preferably, the ratio of xylitol to arabitol produced is about 4.2:1 or more. In other embodiments the ratio of xylitol to arabitol produced in the range of about 4:1 to about 6:1. In yet further embodiments of the invention, the ratio of xylitol to arabitol produced is in the range of about 13:1 to about 20:1. In other preferred embodiments the in the range of about 4:1 to about 20:1. The ratio of xylitol to arabitol may be higher after 24 hours of fermentation time than 48 hours of fermentation time.

The present inventors have advantageously and surprisingly identified a number of inhibitor tolerant *Candida* strains for xylitol production in undetoxified lignocellulosic hydrolysate generated by steam explosion of mild acid impregnated wheat and other straws.

The *Candida* strain may have a mutation or deletion in the first and/or second XYL2 allele. It is preferred that the *Candida* strain has a deletion of the first and/or second XYL2 allele. It is more preferred that the *Candida* strain has a deletion of the first and second XYL2 allele. The genotype of the *Candida* strain may have a genotype selected from one of the following: xyl2-1Δ::SAT1-FLIP; xyl2-1Δ::FRT; xyl2-1Δ::FRT/xyl2-2Δ::SAT1-FLIP; xyl2-1Δ::FRT/xyl2-2Δ::FRT The one or more sugar alcohol may be produced from a lignocellulosic feedstock in a process where maltose is present as a co-substrate. Preferably, maltose is present as the majority co-substrate and there is no or only a minority glycerol co-substrate present in or during the process.

The *Candida* strain may have also been modified so as to express an exogenous amylase. The amylase may be an α-Amylase that hydrolyzes α-1,4 bonds whilst bypassing branched linkages; a ß-Amylase that breaks down α-1, 4 and cannot bypass α-1, 6 branch linkages resulting in maltose generation; γ-Amylase (glucoamylase) that hydrolyzes both α-1, 4 and α-1, 6 linkages consequently releasing monosaccharides as end product.

A number of lignocellulosic feedstocks will be apparent to the skilled addressee, but it will preferably comprise Brewers Spent Grain (BSG) and/or wheat straw hydrolysate. Alternatively, or additionally, the lignocellulosic feedstock may comprise one or more of the following: *miscanthus*, corn stover, corn cobs, oat hulls, willow, sugarcane and bagasse. Where the lignocellulosic feedstock comprises detoxified/undetoxified lignocellulosic hydrolysate, it may be generated by, among other methods (eg dilute acid hydrolysis, ionic liquids, organosolv, ammonia fibre expansion, Karft or sulphonation processes), steam explosion of mild acid impregnated wheat straw.

If the *Candida* strain is derived (or isolated) from a xylophagous organism, such an organism may comprise a beetle. Preferably, such beetles may be a click beetle.

In accordance with another aspect of the present invention, there is provided a method of producing one or more sugar alcohol from a lignocellulosic feedstock, the method comprising: fermenting the lignocellulosic feedstock in the presence of one or more *Candida* strains, as herein above described with reference to the earlier aspects, under conditions sufficient to convert a sugar alcohol precursor into one or more sugar alcohols; and recovering the sugar alcohols.

Preferably, in the method, the one or more sugar alcohols comprises xylitol and arabitol.

During fermentation, it is preferred that maltose is present as a co-substrate. It is also preferred that glycerol is not added as a co-substrate or is only added as a minority component relative to maltose.

The lignocellulosic feedstocks suitable for use in the method will be in a number of formats known to the skilled addressee, but will preferably comprises Brewers Spent Grain (BSG) and/or wheat straw hydrolysate and other feedstocks such as bagasse, *miscanthus*, corn stover, corn cobs, oat hulls, willow, sugarcane.

The method may initially comprise the step of steam exploding mild acid impregnated, among other methods (eg dilute acid hydrolysis, ionic liquids, organosolv, ammonia fibre expansion, Karft or sulphonation processes), wheat straw and other feedstock (eg *miscanthus*, corn stover, corn cobs, oat hulls, willow, sugarcane) so as to form a lignocellulosic feedstock formed of undetoxified lignocellulosic hydrolysate.

The lignocellulosic feedstock may comprise xylose and the xylose to maltose ratio may be in the range of about 2:1 to about 10:1. More preferably, the xylose to maltose ratio may be in the range of about 3:1 to about 9:1. Even more preferably, the xylose to maltose ratio may be in the range of about 4:1 to about 8:1. Yet more preferably, the xylose to maltose ratio may be in the range of about 5:1 to about 7:1. Most preferably, the xylose to maltose ratio may be about 6:1.

The fermentation takes place preferably under aerobic conditions. The fermentation also preferably takes place under elevated aeration conditions.

The fermentation may be a batch, fed-batch or continuous process.

The fermentation may last up to about 70-84 hours. That is to say that depending upon the conditions of the fermentation, the xylose is exhausted towards the end of the batch process.

In accordance with a further aspect of the present invention, there is provided xylitol produced by *Candida* strains, as herein above described and/or as produced using the method as herein above described.

In accordance with a further aspect of the present invention, there is provided a method of modifying a *Candida* strain so as to reduce or prevent the production of arabitol comprising mutating, deleting or attenuating the first and/or second XYL2 allele.

Preferably, the method comprises mutating, deleting or attenuating the first and second XYL2 allele.

In another aspect of the present invention, there is provided a method of producing arabitol from a lignocellulosic feedstock, the method comprising: fermenting the lignocellulosic feedstock in the presence of a *Candida* strain, wherein the *Candida* strain comprises a mutation or deletion in the first and/or second XYL2 allele, under conditions sufficient to convert arabinose into arabitol; and recovering the arabitol. The *Candida* strain may comprises a strain as herein above described.

DETAILED DESCRIPTION OF THE INVENTION

Embodiments of the present invention will now be described, by way of example only, with reference to the following experiments and accompanying figures, in which:

FIG. 1 shows graphs illustrating growth profiles of various newly isolated strains in different mild acid hydrolysates. Four strains were tested and denoted Y6604, Y6603, Y6601 and Y6600 As detailed below, biological deposits for these strains have been made on 6 Jul. 2017, by the Applicant, at the National Collection of Yeast Cultures, Institute of Food Research, Norwich Research Park, Norwich, Norfolk, NR4 7UA, United Kingdom. The strains deposited are as follows: *Scheffersomyces* (*Candida*) *shehatae* (Y6600 (BET3 R660)) NCYC 4187; *Scheffersomyces* (*Candida*) *shehatae* (Y6601 (BET9 R661)) NCYC 4188; *Scheffersomyces* (*Candida*) *shehatae* (Y6603 (NW2 R663)) NCYC 4189; and *Candida tropicalis* (Y6604 (B1020 R664)) NCYC 4190).

Graphs A, B, C and D represent strain behaviour in *Miscanthus* (MG), willow (WW), wheat straw (WS) and corn stover (CS) hydrolysates respectively. Values represent mean $OD_{600}$ of duplicate readings in microtitre plates;

FIG. 2 shows graphs illustrating xylose to xylitol bioconversion by various strains in different mild acid hydrolysates. Strains are represented as Y6600, Y6601, Y6603 and Y6604 (corresponding to NCYC 4187, NCYC 4188, NCYC 4189 & NCYC 4190). Graphs A, C, E and B, D, F show the xylose and xylitol profiles respectively in corn stover (CS), *miscanthus* (MG) and wheat straw (WS) hydrolysates. Values represent the mean of duplicate analysis in shake flasks;

FIG. 3 illustrates a phylogenetic tree drawn using the neighbour-joining method with Kimura two-parameter model based on the D1/D2 domain of the LSU rRNA gene in Y6604 NCYC 4190);

FIG. 4 show graphs illustrating xylose utilisation profiles of Y6604 (NCYC 4190) in the presence of increased inhibitor concentrations. Graphs A, B, C, D, E and F represent strain performance in the presence of increasing concentrations of vanillin (VAN), transcinnamic acid (TRANSC), hydroxyl-benzaldehyde (HBA), syringaldehyde (S), furfural (F) and hydroxyl-methyl furfural (HMF) respectively. Indicated values in the legend represent concentrations in mg/100 mL. Xylose values are the mean of two replicates in minimal media in shake flasks;

FIG. 5 shows a schematic gene map of the deletion of Xyl2 in *C. tropicalis* using the SAT1 flipper. A(i) & A(ii) show the homologous recombination of the Xyl2 deletion cassette with subsequent flipper excision, A(iii) shows leaving behind a single FRT element. A(iv) shows that the whole process was repeated to remove the other Xyl2 copy. Only relevant unique restriction sites have been shown. K, KpnI; Xh, XhoI; ScI, SacI; SpI, SphI. (B) shows PCR verification of the deletion of one (AXyl2; Lane 2) and two (AAXyl2; Lane 3) alleles at the Xyl2 locus using primers 63/64. ORF deletion yielded a lower band size compared to the WT (lane 1) when amplified with primers located within the Xyl2 flanks. (C) shows RT-PCR based evaluation of Xyl2 gene copy numbers in WT and mutants using primers RT-PCR FP1/RP1. Values represent the mean with vertical error bars representing the standard deviation (n=3). (D) shows growth of *C. tropicalis* Y6604 (WT) (NCYC 4190) (quadrant 1), heterozygous (2,3) and homozygous (4,5) Xyl2 mutants with (2,4) or without (3,5) the customised SAT1 deletion construct in minimal media (YNB-Xylose agar);

FIG. 6 shows graphs comparing the impact of Xyl2 deletion upon fermentation profiles in synthetic media and WS hydrolysate (WSH). Graphs A/D, B/E and C/F represent the profiles for Y6604 (*Candida tropicalis* NCYC 4190), ΔXyl2 (also referred to as NCYC 4185 or Y6604 X1) and ΔΔXyl2 (also referred to as NCYC 4186 or Y6604 X2) in YEP media and WSH respectively. TMS stands for Total Minor Sugars and encompasses glucose, galactose, fructose and mannose. Values represent the mean of duplicate experiments and error bars indicate one standard deviation;

FIG. 7 shows graphs illustrating the effects of various co-substrates upon ΔΔXyl2 fermentation in minimal media (YNB) and wheat straw hydrolysate (WS). Graphs represent changes in indicated co-substrate (A and B), cell growth (C and D) and consequent utilisation of xylose (E and F) in minimal media (A, C and E) or wheat straw hydrolysate (B, D and F), arabitol accumulation following addition of various co-substrates during ΔΔXYL2 fermentations in WSH (G). Values represent the mean of two independent replicates and error bars represent one standard deviation;

FIG. 8 shows graphs illustrating the Optimisation of co-substrate addition for xylose conversion by ΔΔXyl2 in wheat straw hydrolysate. Graphs A and B represent alterations in cellular growth and extracellular xylose respectively following WSH supplementation with indicated amounts of glycerol or maltose. Values represent the mean of two independent replicates and error bars represent one standard deviation;

FIG. 9 shows a graph illustrating the xylose to xylitol conversion profile by ΔΔXyl2 using wheat straw hydrolysate in bioreactors. Experiments were conducted in a 2 L bioreactor (working volume 1 L) at 30° C. with continuous agitation (200 rpm), aeration (1.5 vvm) and no pH control. Values represent the mean of two independent replicates and error bars represent one standard deviation;

FIG. 10 shows graphs illustrating xylitol production by ΔΔXyl2 in optimised batch (graph A) and fed-batch (graph B) cultures in wheat straw hydrolysate. Experiments were conducted in a 2 L bioreactor (working volume 1 L) at 30° C. with continuous agitation (200 rpm), aeration (1.5 vvm) and no pH control. Values represent the mean of two independent replicates and error bars represent one standard deviation;

FIG. 11 shows a graph illustrating the fermentation profile of ΔΔXyl2 in 45 L of wheat straw hydrolysate. Values represent the mean of duplicate biological samples from the same fermenter. Vertical bars represent standard deviation from the mean;

FIG. 12 shows a graph illustrating the fermentation profile of ΔΔXyl2 in 140 L of wheat straw hydrolysate. Area beyond the dotted lines in graphs AB represents fermentation characteristics after the maltose spike. Values represent the mean of duplicate biological samples from the same fermenter. Vertical bars represent standard deviation from the mean;

Figure 15:
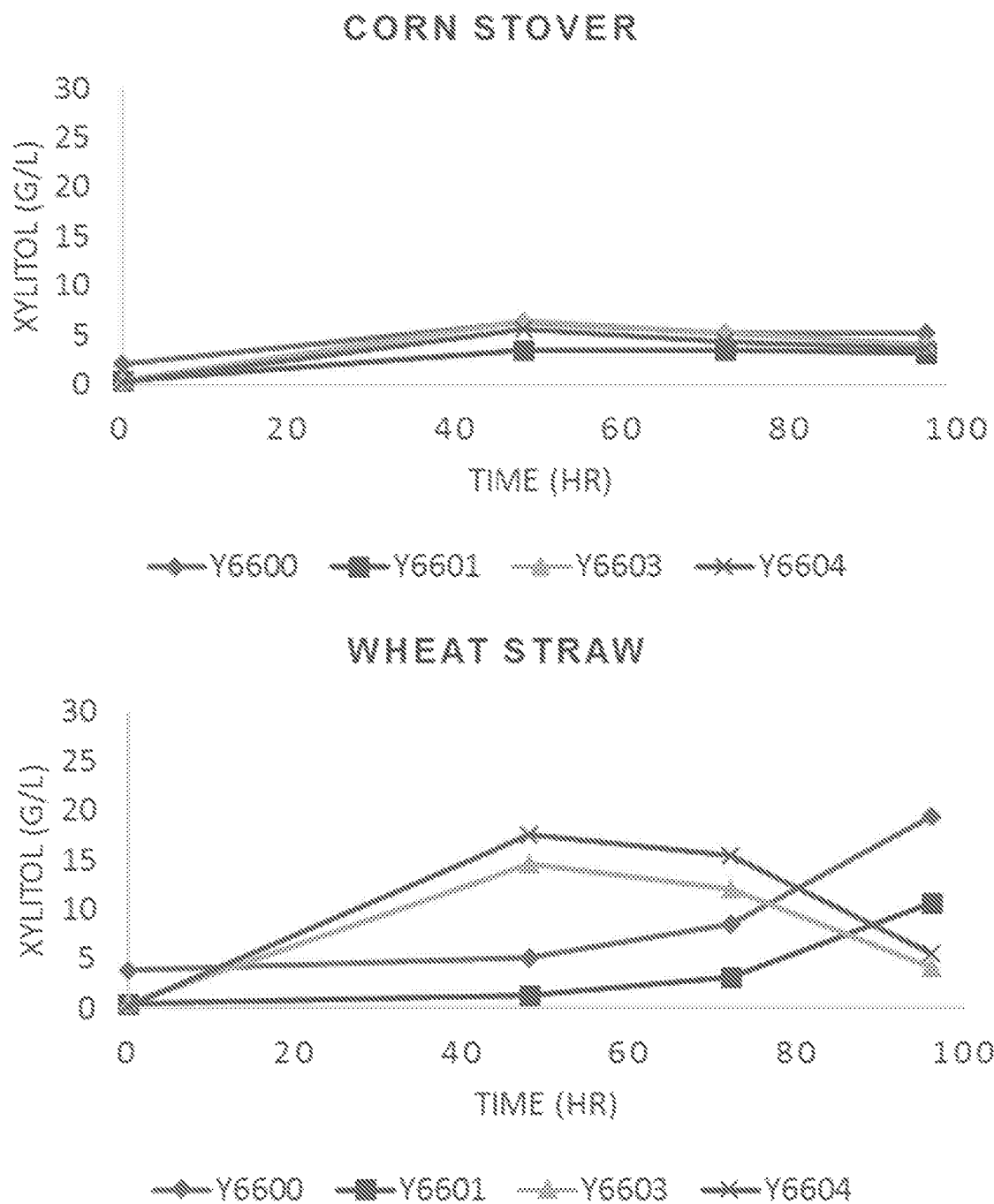
Figure 15:
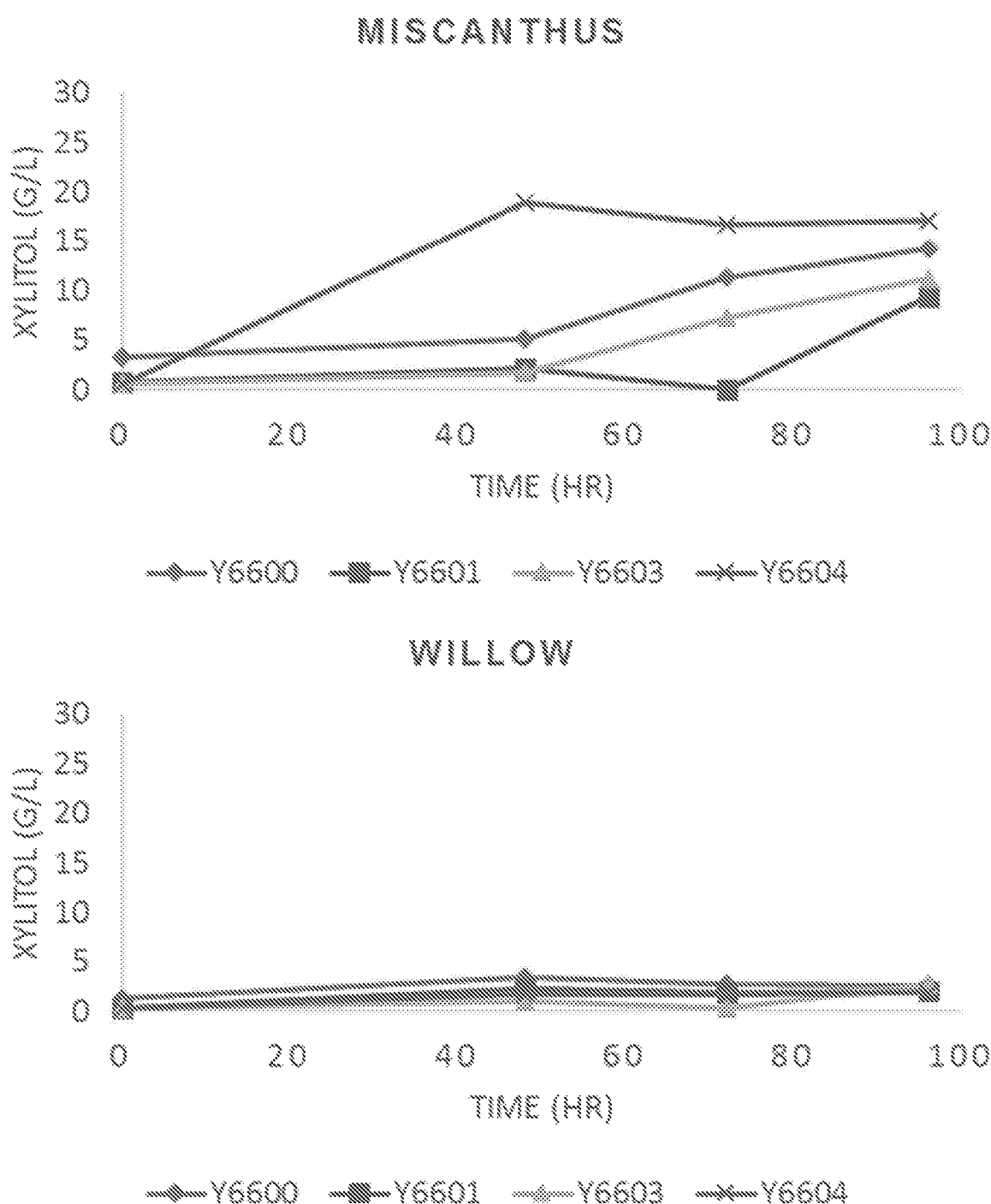
Figure 16:
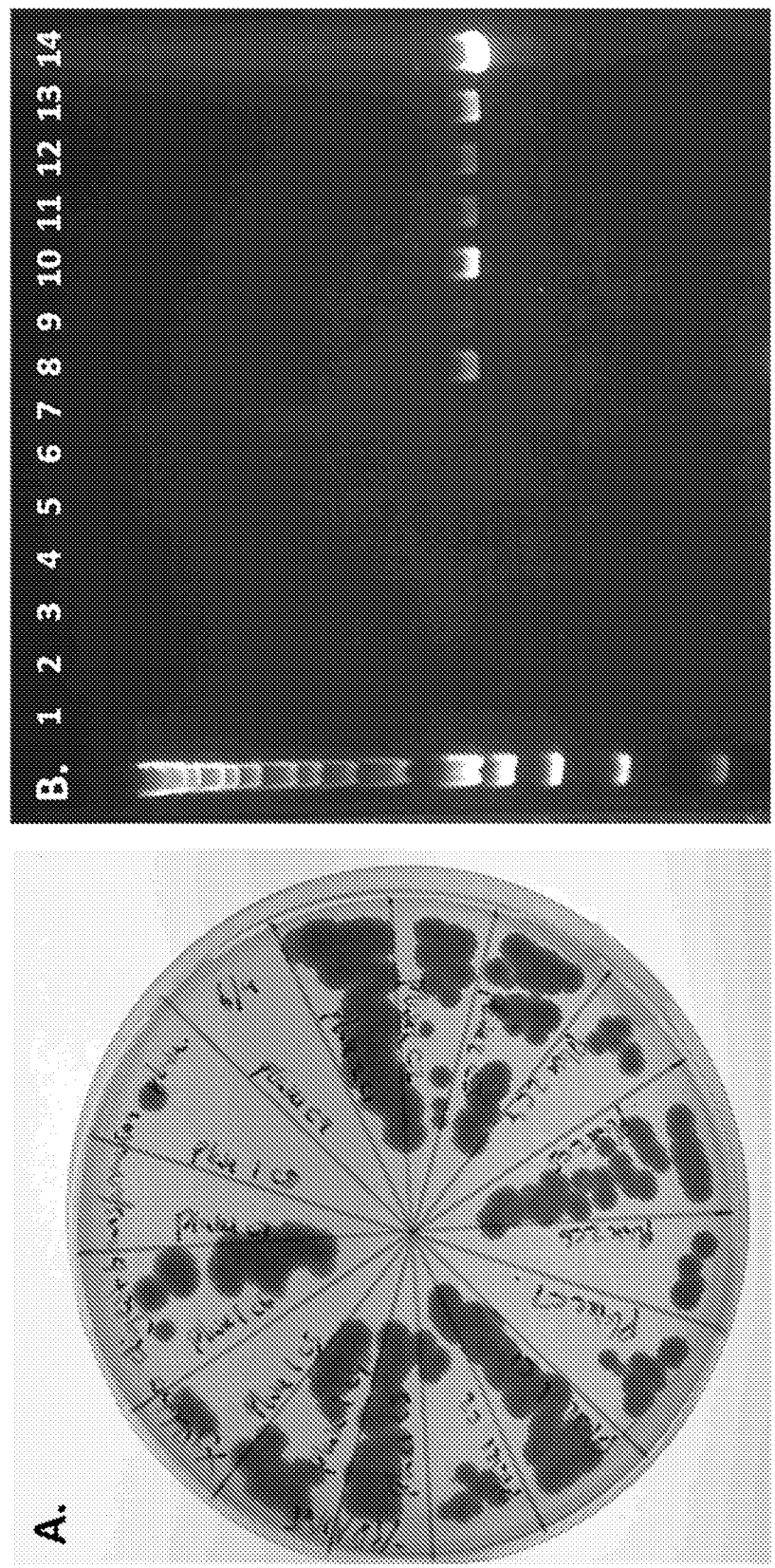

FIG. 15 shows graphs illustrating xylitol production by the four isolated *Candida* strains in different lignocellulosic hydrolysates. All hydrolysates were generated following steam explosion of mild acid pre-treated lignocellulosic feedstock; and FIG. 16 shows the Transformation of *Scheffersomyces* (*Candida*) *shehatae* Y6600 (NCYC 4187) with linear DNA from pΔXYL2Y6600 to delete one of the XYL2 alleles. (A) Nou$^r$ colonies obtained following Y6600 transformation. (B) Gel image following colony PCR of some of the Nou$^r$ colonies using primers Y6600Xyl2deletioncheck-FP/-RP. Lanes 8-14 are positive controls using the same DNA template but a different primer set.

YEAST STRAIN AND CULTURE CONDITIONS

*Candida tropicalis* and *Scheffersomyces* (*Candida*) *shehatae* strains used in current study are listed in Table 1 below.

TABLE 1

| Strains | Parent | Relevant Genotype |
|---|---|---|
| Y6601 - NCYC 4187 | | Wild Type strain |
| Y6602 - NCYC 4188 | | Wild Type strain |
| Y6603 - NCYC 4189 | | Wild Type strain |
| Y6604 - NCYC 4190 | | Wild Type strain |
| Y66041 | NCYC 4190 | xyl2-1Δ::SAT1-FLIP |
| Y6604 X1 - NCYC 4185 | Y66041 | xyl2-1Δ::FRT |
| Y66043 | NCYC 4185 | xyl2-1Δ::FRT/ xyl2-2Δ::SAT1-FLIP |
| Y6604 X2 - NCYC 4186 | Y66043 | xyl2-1Δ::FRT/ xyl2-2Δ::FRT |

For creation of gene deletion mutants, representative colonies were grown in YPD (1% yeast extract, 2% neutralized bacteriological peptone and 2% dextrose), at 30° C. and under continuous agitation at 200 rpm. These were then maintained on YPD agar. For the selection of nourseothricin-resistant colonies, YPD agar (1% yeast extract, 2% neutralized bacteriological peptone, 2% dextrose and 2% agar; all in w/v) was supplemented with 200 μg/mL nourseothricin (Jena Biosciences, Germany) whilst removal of the gene deletion cassette was achieved by cellular growth in YPM medium (1% yeast extract, 2% neutralized bacteriological peptone and 2% maltose).

When assessing microbial ability for xylitol production in synthetic media, WT and deletion mutants were grown in YEP (5% xylose, 0.1% arabinose, 0.025% glucose, 1% yeast extract, 2% peptone, 0.05% $MgSO_4$, 0.05% $KH_2PO_4$, 0.02% $ZnSO_4$ and 0.02% $ZnSO_4$; all w/v) whilst comparison of different additives as suitable co-substrates was accomplished in YNB-Xylose (Yeast Nitrogen Base with amino acids and 5% xylose) supplemented separately with individual compounds. WSH was provided by Beacon Pilot Facility, Aberystwyth University and a suitable nitrogen source (1% yeast extract, 2% peptone, 0.05% $MgSO_4$, 0.05% $KH_2PO_4$, 0.02% $ZnSO_4$ and 0.02% $ZnSO_4$; all w/v).

The impact of XYL2 deletion on arabitol generation was investigated in YEP base medium containing glucose (1%, w/v) along with similar amounts of xylose (4%, w/v) and arabinose (3.5%. w/v).

As detailed below, biological deposits for these strains have been made on 6 Jul. 2017, by the Applicant, at the National Collection of Yeast Cultures, Institute of Food Research, Norwich Research Park, Norwich, Norfolk, NR4 7UA, United Kingdom. The strains deposited are as follows: *Candida tropicalis* (Y6604 X1) NCYC 4185; *Candida tropicalis* (Y6604 X2) NCYC 4186; *Scheffersomyces* (*Candida*) *shehatae* (Y6600 (BET3 R660)) NCYC 4187; *Scheffer-*

*somyces* (*Candida*) *shehatae* (Y6601 (BET9 R661)) NCYC 4188; *Scheffersomyces* (*Candida*) *shehatae* (Y6603 (NW2 R663)) NCYC 4189; and *Candida tropicalis* (Y6604 (B1020 R664)) NCYC 4190.

Plasmids and Strain Construction

Targeted gene deletion in Y6604 (NCYC 4190) was accomplished using the SAT1 flipper system provided by University of Würzburg within the plasmid pSFS2a (ReuB et al. 2004). For deletion of the first XYL2 allele, 500 base pairs upstream and downstream of the open reading frame (ORF) were PCR amplified from Y6604 (NCYC 4190) genomic DNA using primers Xyl2 −500 FP/Xyl2 0 RP and Xyl2+1095 FP/Xyl2+1566 RP respectively (oligonucleotides are listed in Table 2 below).

TABLE 2

| Primer Name | Sequence | SEQ ID |
|---|---|---|
| Xyl2 - 500 | ggtggtggtaccTGTTTTGGAATTCAATTTTCCC | 1 |
| Xyl2 0 | ggtggtctcgagTGACTTTTGTATTTGTAGAATTGAAAG | 2 |
| Xyl2 + 1095 | ggtggtgagctcAGGTATATAGTATTAGAAAAAGAATATACAGTATAT | 3 |
| Xyl2 + 1566 | ggtggtgcatgcAATAAATCTTGTATACCAAATTTCTTAGC | 4 |
| Xyl2 + 59 FP | cggggtaccCGAAGCTCCAAAACTCGAATCA | 5 |
| Xyl2 + 372 RP | tccgctcgagCATCTGGGTTAACTGGTGGG | 6 |
| Xyl2 + 749 FP | ggtgagctcGGAATGTAGTGGTGCTCAACC | 7 |
| Xyl2 + 1061 RP | acatgcatgcACCATTTCCTGCTCTGACCAA | 8 |
| Xyl2 Primer 63 | TGAATAGATTGTAGGACCTTGGCA | 9 |
| Xyl2 Primer 64 | TCCTTGGCCTTCATTCTTGCT | 10 |
| Xyl2RT-FP1 | AACCCAGATGAACCAAATCC | 11 |
| Xyl2RT-RP1 | ACCGTGGACACCAACAGTTA | 12 |
| Ura3RT-FP1 | TATTGCTCAACGTGATATGG | 13 |
| Ura3RT-RP1 | GTTGACCTAAAGCATCACCT | 14 |

Figure 5:
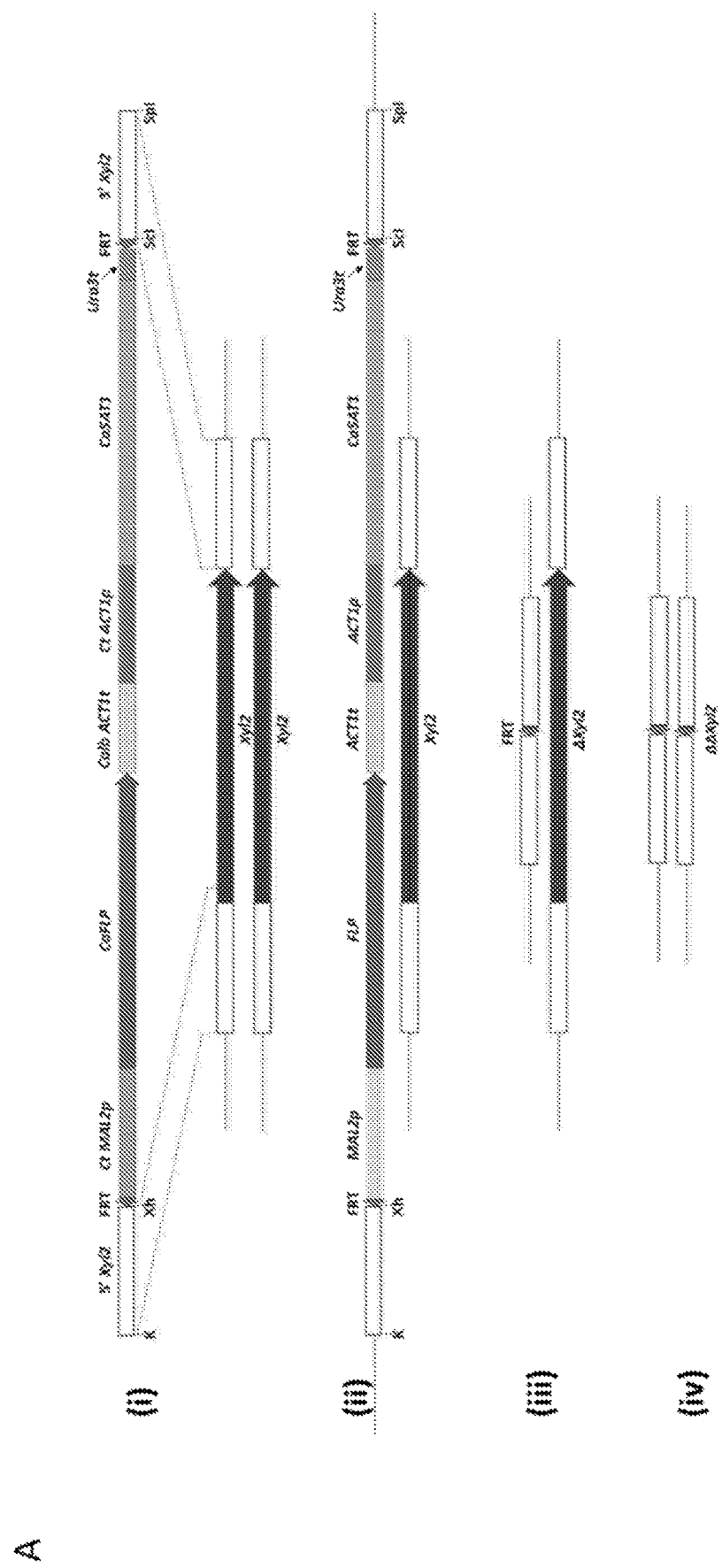
Figure 5:
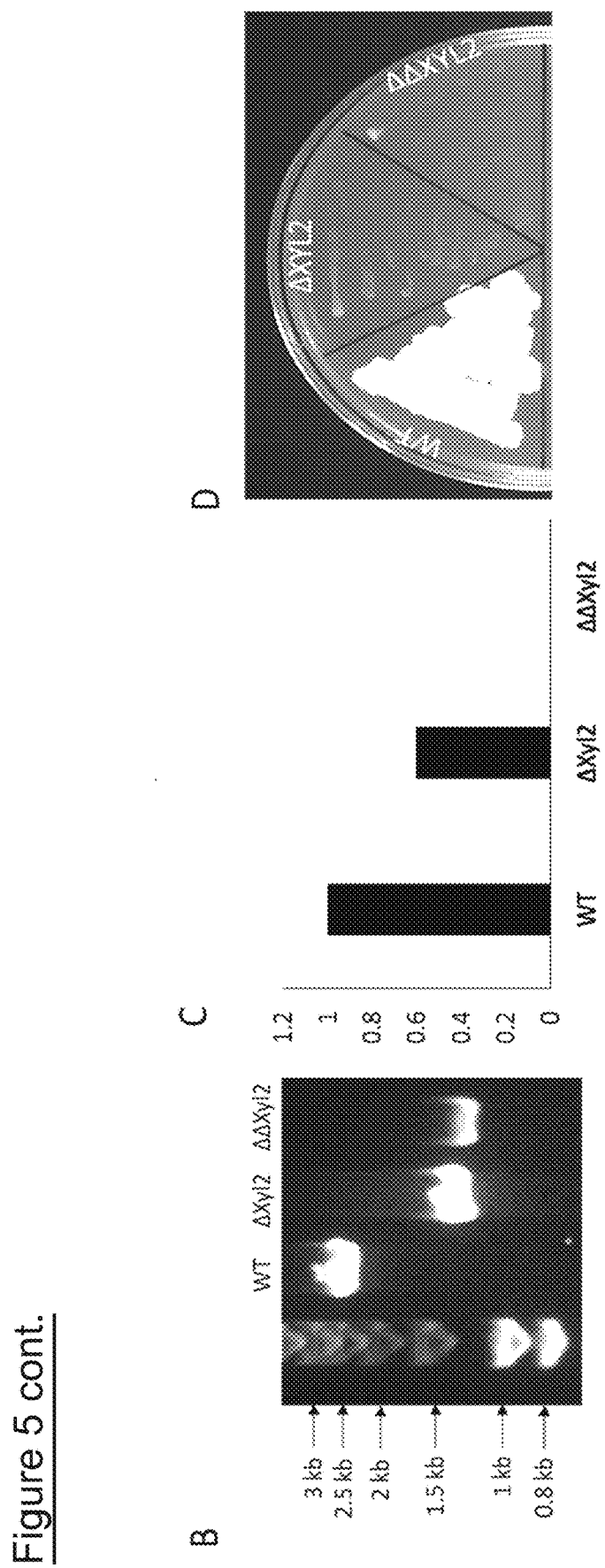

The upstream and downstream fragments were digested with KpnI/XhoI and SacI/SphI whilst the SAT1 flipper harbouring plasmid pSFS2a was digested with XhoI/SacI. All fragments were ligated within a pUC19 vector backbone (digested with KpnI/SphI) in a single quadruple ligation reaction. The resulting plasmid was designated as pΔXyl2A and digested with KpnI/SphI to liberate the first Xyl2 deletion cassette (as shown in FIG. 5A(i)). For removal of the second Xyl2 allele, upstream fragment was amplified using primers Xyl2+59 FP/Xyl2+372 RP whilst Xyl2+749 FP/Xyl2+1061 RP were used for the downstream flank. The procedure for ligation cloning of the two flanks and SAT1 flipper within pUC19 was repeated to generate plasmid pΔXyl2B and consequently the respective deletion cassette obtained via double digestion.

*C. tropicalis* strains were transformed as described previously (Porman et al. 2013; Seervai et al. 2013) with slight modifications in the integrative electroporation protocol. In brief, following initial growth in YPD, cells were treated with lithium acetate (0.1 M), Tris-HCl (7.5 mM, pH 8), EDTA (1 mM) and dithiothreitol for 1 hr at room temperature. Henceforth cells were subjected to two water and one sorbitol (1 M) washes, final resuspension being in leftover sorbitol following decantation. For each transformation, approximately 50 μL of cell suspension was mixed with 10-15 μL of linear DNA in 0.2 cm sterile electroporation cuvettes and electroporated at 1.8 kV using Gene Pulser II electroporation system (BioRad). Immediate resuspension of the cells in pre warmed YPD (1 mL) was followed by cellular recovery for 4 hr at 30 C. Cells were eventually spread on YPD containing 200 μg/mL nourseothricin and incubated at 30° C. for 24-48 hr to screen for cells that had successfully undergone homologous recombination to replace the gene of interest with the deletion cassette. Specific integration was confirmed via PCR using primer pairs binding within the cassette and either up- or downstream of the target locus (oligonucleotides are listed in Table 2). In order to flip the SAT1 marker out from the integration site, nourseothricin resistant colonies were grown in YPM at 30° C. for 1-2 days with subsequent replica patching to YPD plates with and without nourseothricin. Loss of the deletion cassette was confirmed by PCR using Xyl2 primers 63/64 binding within the gene's flanking regions. For double mutants the transformation and flipper removal process was repeated with appropriate deletion cassettes followed by PCR confirmation of ORF removal (FIG. 5B).

Real-Time PCR

For confirming the removal of Xyl2 alleles real time PCR was performed using the $\Delta\Delta C_t$ method (Livak and Schmittgen 2001). DNA was isolated from overnight cultures of WT and Xyl2 deletion mutants using a RiboPure DNA isolation kit (ZymoResearch, USA). RT-PCR was conducted using the SyBr green Master Mix (Fisher, UK) with Ura3 as the housekeeping gene. Amplification of Ura3 and Xyl2 was performed using the primer pairs Ura3RT-FP1/-RP1 and Xyl2RT-FP1/-RP1 respectively on a Roche 486 cycler (Roche Diagnostics, UK). Initial denaturation at 95° C. for 2 min was followed by 30 PCR cycles (95° C. for 15 s, 55° C. for 30 s, 72° C. for 15 s). Amplicon specificity was determined by melt curve analysis and amplification of Xyl2 has been presented after normalization against the Ura3 control. Gene copy number values represent the mean of three independent replicates.

Comparison of Xylitol Production in Shake Flasks

To compare the impact of Xyl2 deletion upon xylose to xylitol bioconversion and for assessing co-substrate efficacy with the double deletion mutant, shake flask fermentations were conducted in Erlenmeyer flasks (250 mL) containing 100 mL of fermentation medium that was continuously agitated at 200 rpm at 30° C. Pre-cultures grown in YPD were used for inoculation at starting $OD_{600}$ of 0.1-0.2. Strain performance was assessed in both synthetic media and WSH. When optimising co-substrate feed within WSH, 0.5%, 1% and 1.5% of glycerol and maltose were added to WSH containing around 3% xylose to yield substrate:co-substrate ratios of 1:6, 1:3 and 1:2 respectively.

WSH was pasteurized by maintaining in a water bath at 60° C. for 20-25 min followed by chloramphenicol addition (50 μg/mL) and storage at 4° C. until use. Periodic aseptic sampling was performed following which samples were immediately centrifuged and supernatant stored at −20 C until analysis. All experiments were performed in duplicates.

Assessing Xylitol Production from Wheat Straw Hydrolysate in Bioreactor

Larger-scale fermentations were conducted in Infors bioreactors (Techfors-S, Infors HT, Switzerland) with a working capacity of 1 L and equipped for continuous pH, temperature and dissolved oxygen (DO) monitoring. For each bioreactor, a pH probe (Mettler-Toledo, U.K) was calibrated before sterilization and an electrode (TruDO, Finesse, Switzerland) for measuring dissolved oxygen (DO) was calibrated in situ post sterilization by flushing nitrogen (0% calibration) followed by air (100% calibration). Xylitol production was achieved by cell culturing at 30° C., 200 rpm and aeration at 1.0 L/min without any pH control in undetoxified, concentrated WSH with nitrogen (as described earlier) and maltose (1% w/v). The optimised fermentation regime for Xyl2 double mutant in concentrated WSH (with nitrogen as earlier) was conducted at 30° C., 200 rpm, aeration at 2.0 L/min and increased inoculum at the beginning (starting $OD_{600}$ of 0.8). For bioreactor cultures, undetoxified WSH was not pasteurized and only chloramphenicol (50 μg/mL) was added.

Fermentation Conditions

Figure 6:
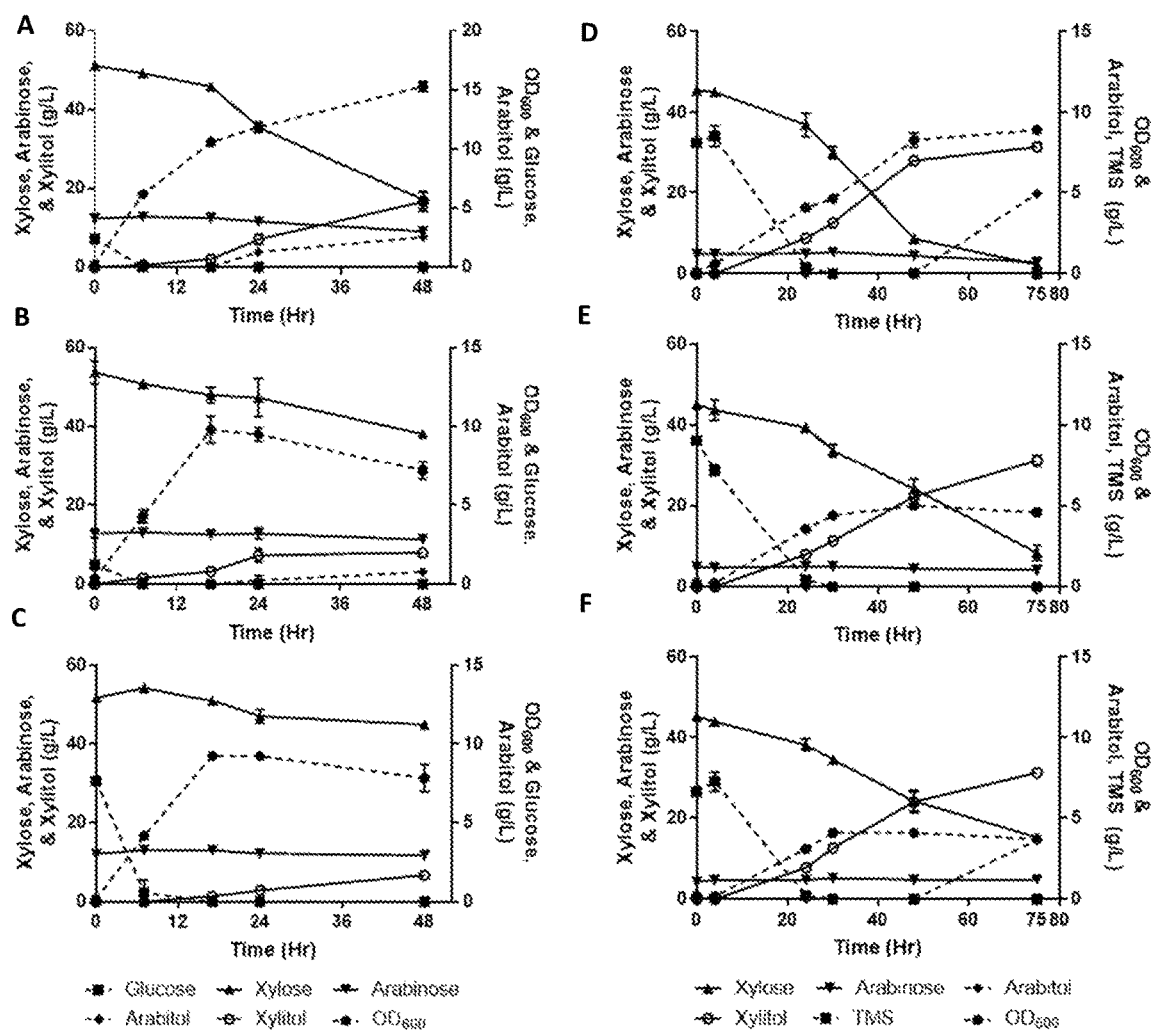
Figure 7:
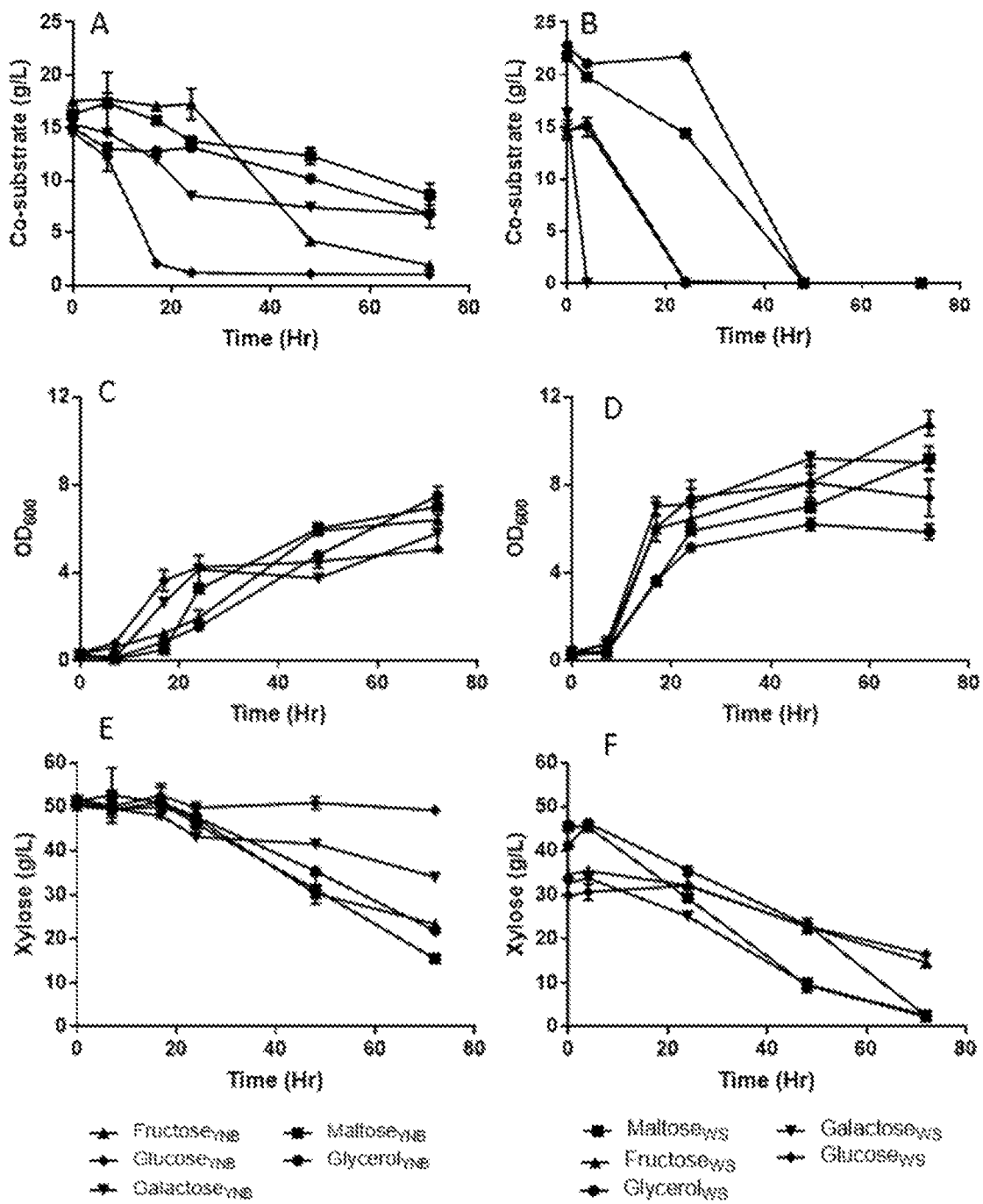
Figure 7:
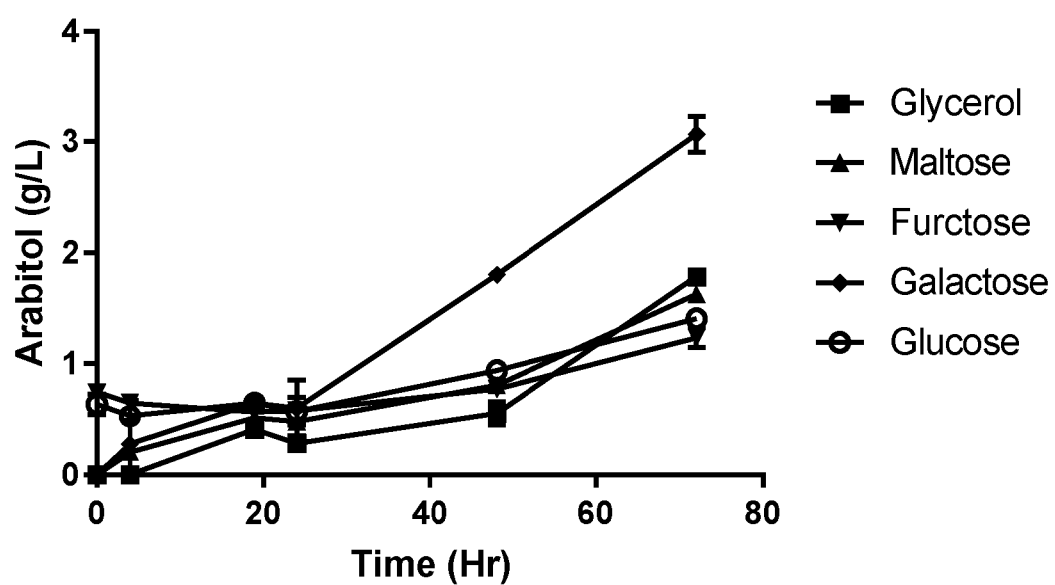
Figure 8:
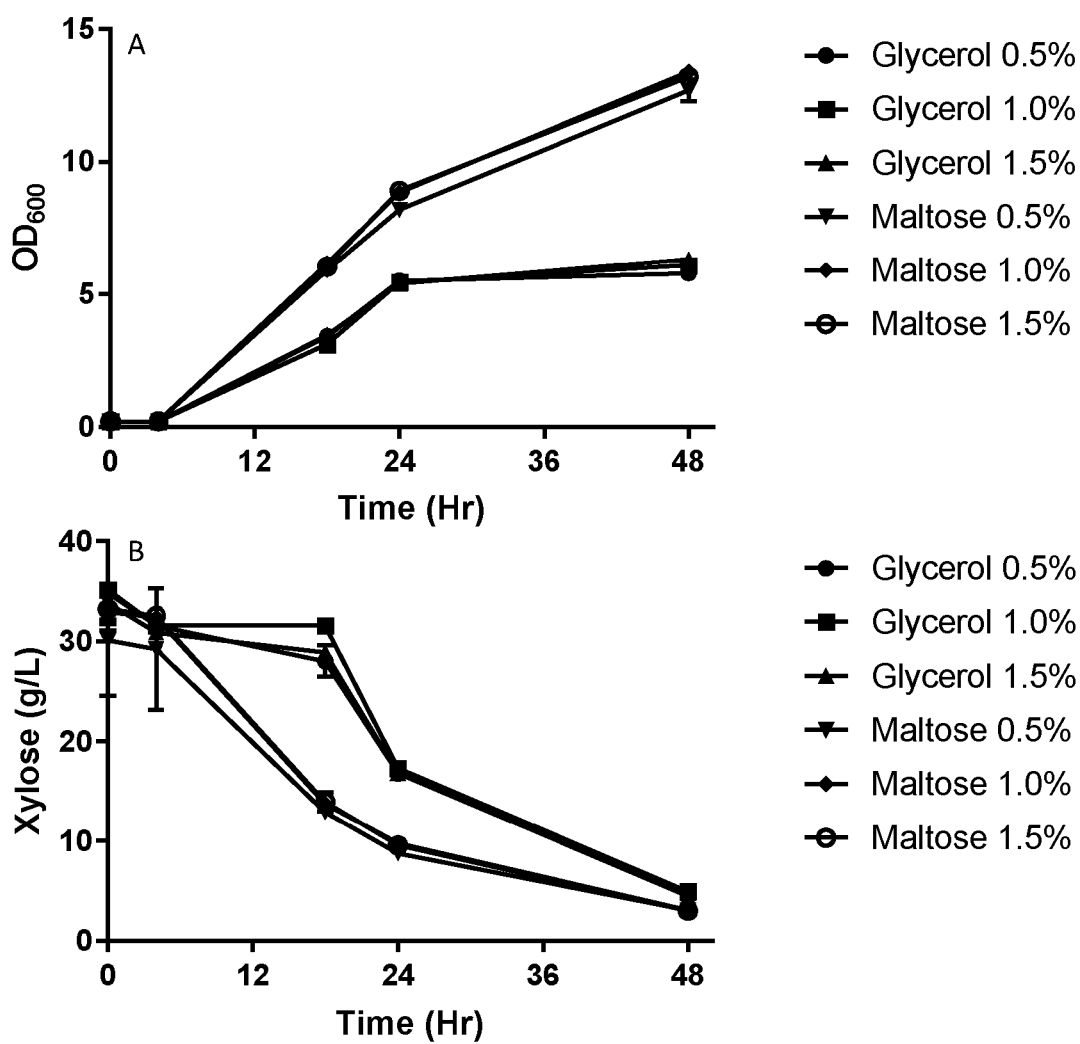

Fermentation conditions FIGS. 6, 7 & 8. To compare the impact of Xyl2 deletion upon xylose to xylitol bioconversion and for assessing co-substrate efficacy with the double deletion mutant, shake flask fermentations were conducted in Erlenmeyer flasks (250 mL) containing 100 mL of fermentation medium that was continuously agitated at 200 rpm at 30° C. Pre-cultures grown in yeast potato dextrose (YPD) were used for inoculation at starting $OD_{600}$ of 0.1-0.2. Strain performance was assessed in both synthetic media and wheat straw hydrolysate (WSH). When optimising co-substrate feed within WSH, 0.5%, 1% and 1.5% of glycerol and maltose were added to WSH containing around 3% xylose to yield substrate:co-substrate ratios of 1:6, 1:3 and 1:2 respectively.

When assessing microbial ability for xylitol production in synthetic media, WT and deletion mutants were grown in YEP (5% xylose, 0.1% arabinose, 0.025% glucose, 1% yeast extract, 2% peptone, 0.05% $MgSO_4$, 0.05% $KH_2PO_4$, 0.02% $ZnSO_4$ and 0.02% $ZnSO_4$; all w/v) whilst comparison of different additives as suitable co-substrates was accomplished in YNB-Xylose (Yeast Nitrogen Base with amino acids and 5% xylose) supplemented separately with individual compounds (namely fructose, glucose, galactose, maltose or glycerol). WSH was prepared in the Beacon Pilot Facility, Aberystwyth University and a suitable nitrogen source (1% yeast extract, 2% peptone, 0.05% $MgSO_4$, 0.05% $KH_2PO_4$, 0.02% $ZnSO_4$ and 0.02% $ZnSO_4$; all w/v) was used for WSH fermentations.

Figure 9:
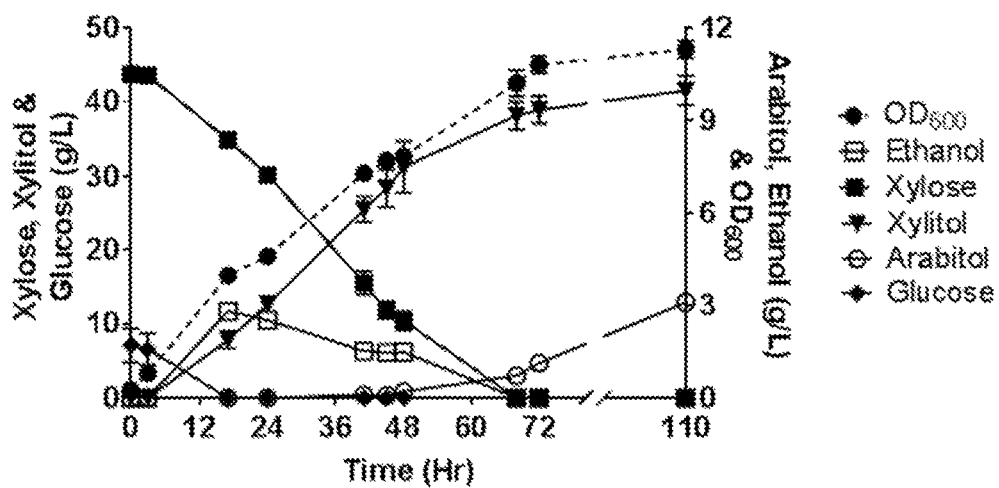

Fermentation conditions FIG. 9. Benchtop scale bioreactor fermentations were conducted in 1.3 L Labfors bioreactors (Infors AG, Switzerland) with a working capacity of 1 L and equipped with two Rushton turbine impellers and probes for continuous pH (K8, Finesse, Chur, Switzerland), temperature and dissolved oxygen (DO) (OxyFerm FDA 225, Hamilton, Bonaduz, Switzerland) monitoring. For each bioreactor, the pH probe was calibrated before sterilization and DO electrode was calibrated in situ post sterilization by flushing nitrogen (0% calibration) followed by air (100% calibration). Xylose to xylitol bioconversion using ΔΔXYL2 were achieved by cell culturing at 30° C., 200 rpm and aeration at 1 vvm without any pH control in undetoxified YEP-WSH (4.4% xylose, w/v) containing maltose (0.7% w/v).

Figure 10:
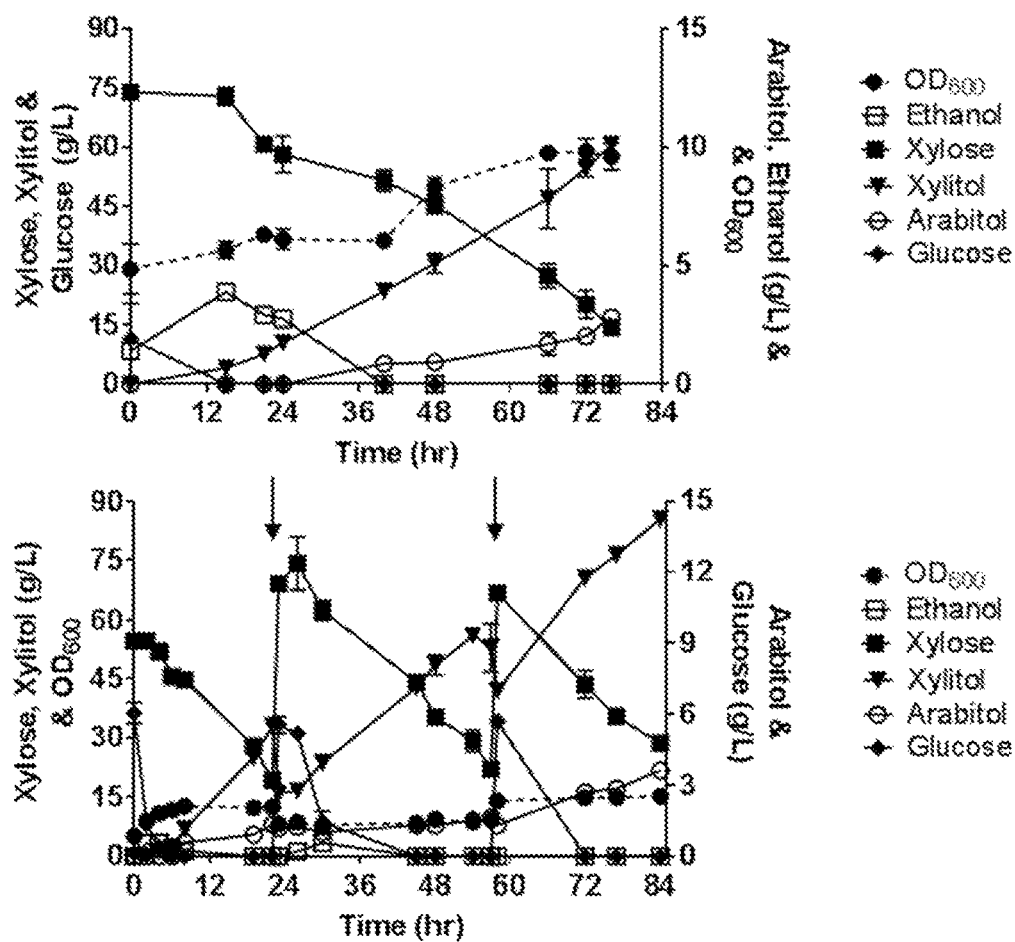

Fermentation conditions FIG. 10 (top chart). The optimised fermentation regime for ΔΔXyl2 double mutant in concentrated WSH with maltose (1.3% w/v; final xylose: maltose ratio of 1:6) & nitrogen (as earlier) was conducted at 30° C., 200 rpm, aeration at 1.5 L/min and increased inoculum at the beginning (starting $OD_{600}$ of 5). For bioreactor cultures, undetoxified WSH was not pasteurized and only chloramphenicol (50 μg/mL) was added.

Fed-batch fermentation conditions FIG. 10 (bottom chart). Fed-batch fermentations were conducted in 1 L Infors bioreactors with 0.3 L of WSH (supplemented with maltose (xylose:maltose ratio of 1:6) and nitrogen source (1% yeast extract, 2% peptone, 0.05% $MgSO_4$, 0.05% $KH_2PO_4$, 0.02% $ZnSO_4$ and 0.02% $ZnSO_4$; all w/v). The culture conditions such as temperature, inoculum size, agitation rate and aeration levels were the same as those of batch fermentation. When leftover xylose reached between 15-20 g/L, concentrated WSH (supplemented with maltose and nitrogen source) was added after 22 h and 57 h to yield a final xylose concentration of more than 67 g/L and total reactor volumes of 0.7 L and 1 L respectively. Samples were removed at regular intervals to determine levels of investigative compounds.

Figure 11:
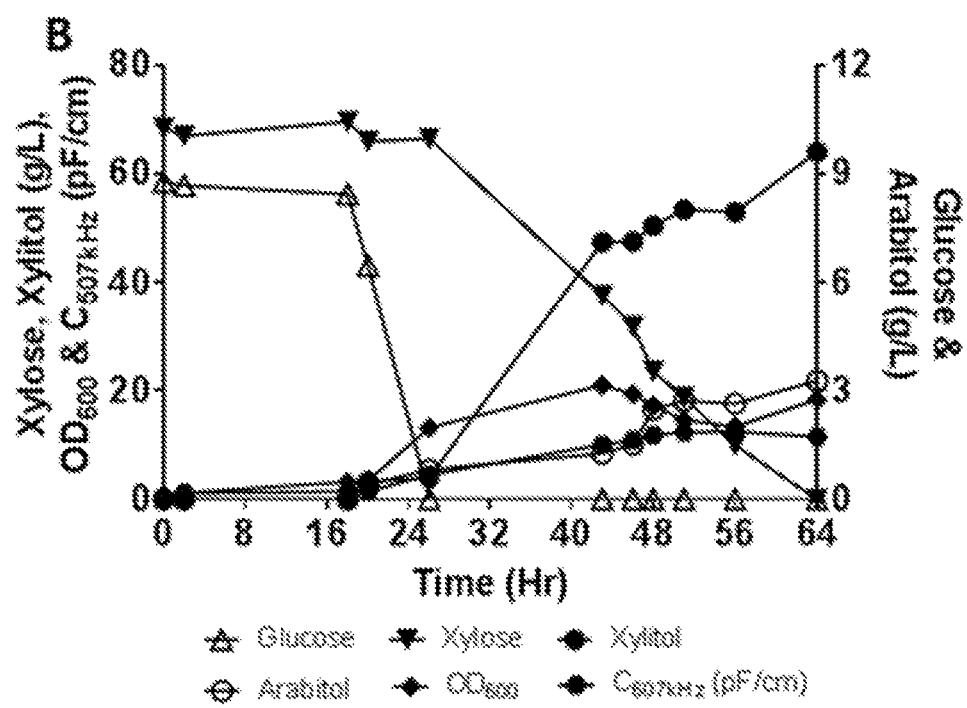

Fermentation conditions FIGS. 11 (45 L) & 12 (140 L). Scaled-up batch fermentations were conducted in 45 L and 140 L of concentrated WSH respectively with starting xylose concentrations of 7% and 5.7% (w/v) respectively. WSH was supplemented with maltose (around 1.2% and 1% respectively) and nitrogen source. Unlike previous smaller-scale WSH fermentations, a cheaper nitrogen source was utilized for scaled-up fermentations and constituted of peptone (1%; w/v), urea (1.8%; w/v) along with other rare minerals which were unchanged (0.05% $MgSO_4$, 0.05% $KH_2PO_4$, 0.02% $ZnSO_4$ and 0.02% $ZnSO_4$). For both 45 L and 140 L, fermentations were conducted with Y4ΔΔXyl2 under aerobic conditions with continuous agitation (200 rpm) and air supply of 70 L/min or 210 L/min respectively yielding final aeration at 1.5 vvm. The temperature was constantly maintained at 30° C. whilst the inoculum size was kept at a starting $OD_{600}$ of around 0.8-1. WSH pH was not maintained during the process and ranged between 5-5.5 at the start of fermentation. Samples were collected at regular intervals and spun at 8000 rpm. Pellets were snap frozen in liquid nitrogen and stored at −80° C. whilst supernatant was filter sterilized and stored at −20° C.

Analytical Methods

To avoid co-elution between the different compounds, samples were run on different HPLC columns equipped with varied detectors. Sugar analysis including quantification of xylose, glucose, arabinose, fructose, galactose and mannose was performed on a SA10 column maintained at 30° C. with water as the mobile phase flowing at 1 mL/min coupled to an L-PAD detector. Separation of xylitol, glycerol and maltose was achieved via a Hi-Plex Ca (duo) 300*6.5 mm column (Agilent, UK) maintained at 75° C. with water flowing at 0.6 mL/min. Arabitol was quantified on an Aminex HP87 column attached to an RI detector with 5 mM $H_2SO_4$ flowing at 0.6 mL/min. Cell growth was monitored by measuring the optical density at 600 nm.

Isolation and Characterisation of a New *Candida tropicalis* Strain

Figure 1:
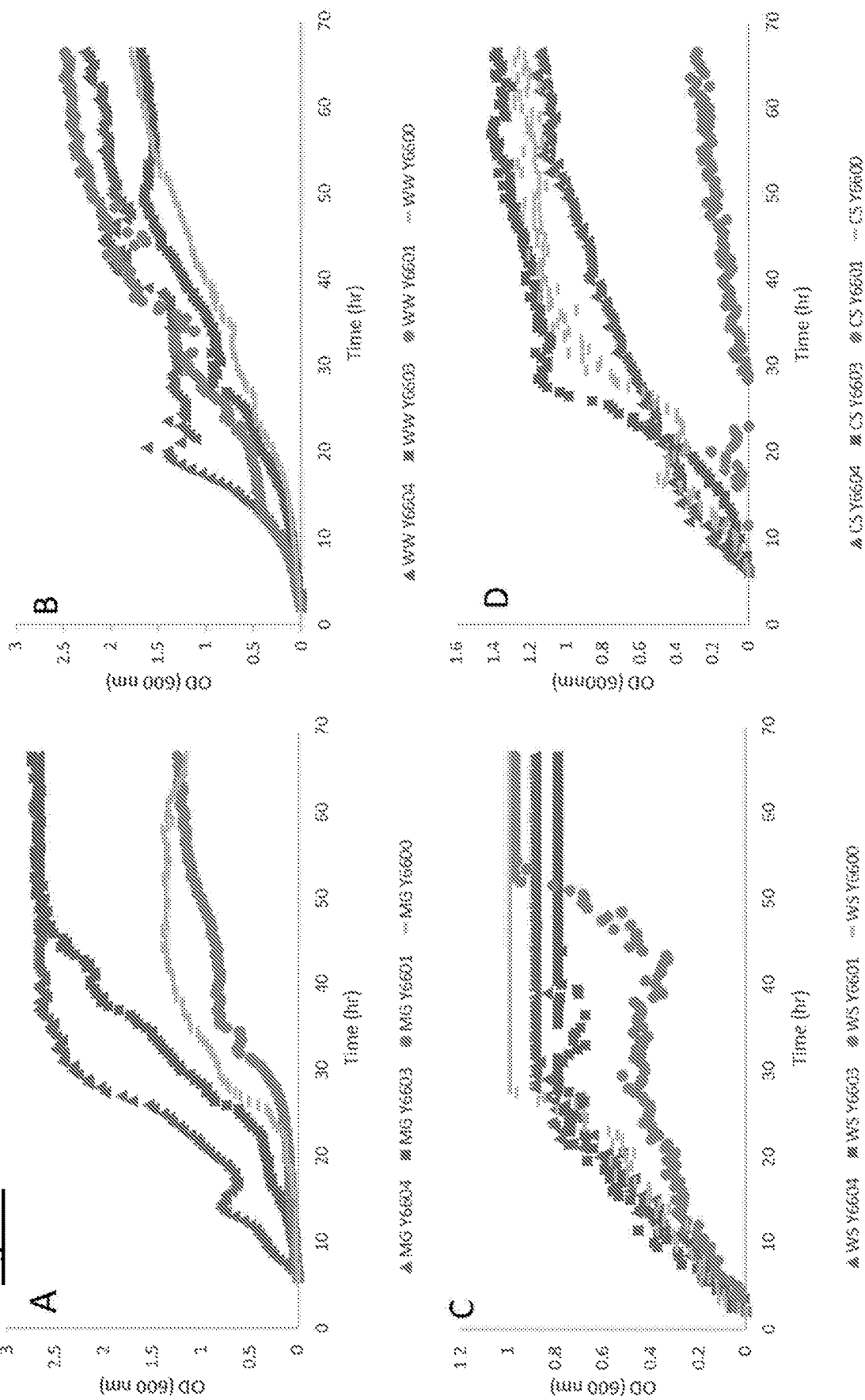
Figure 2:
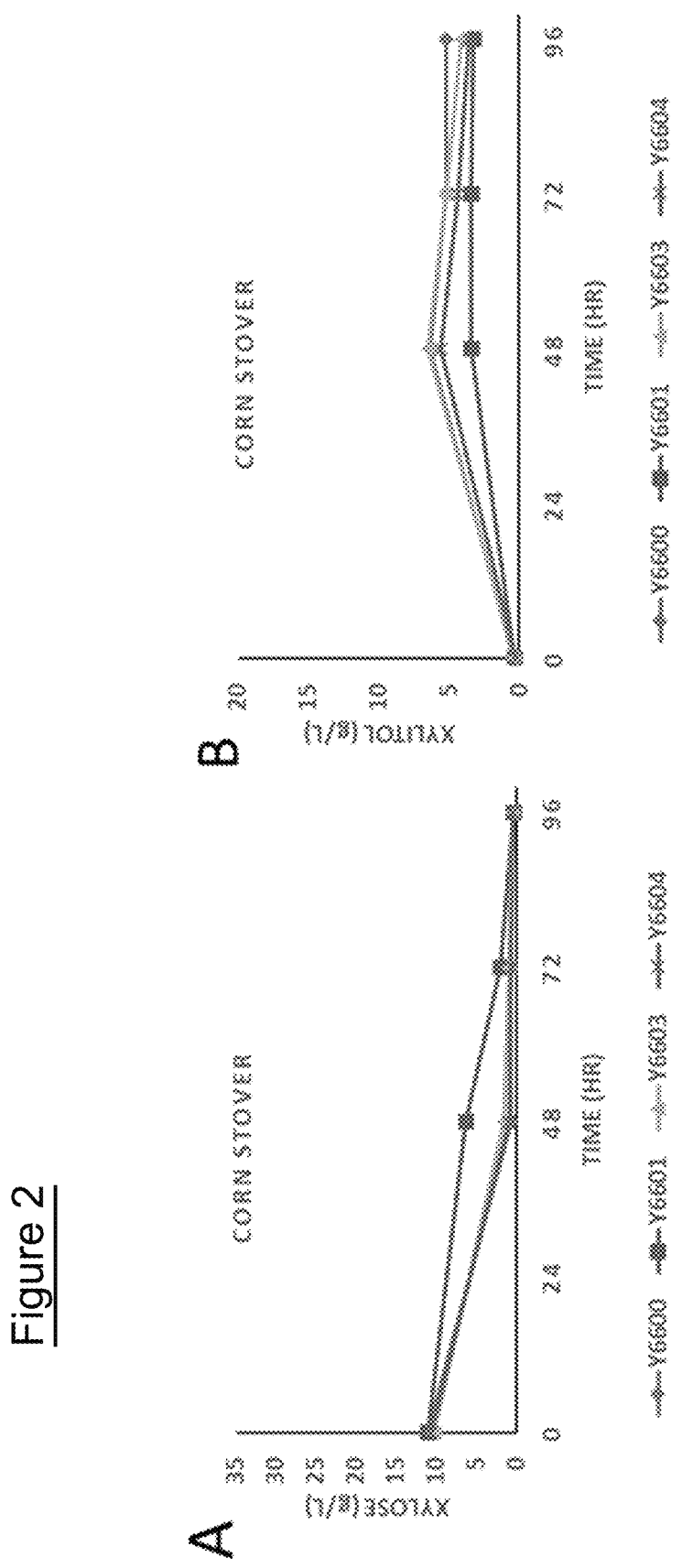
Figure 2:
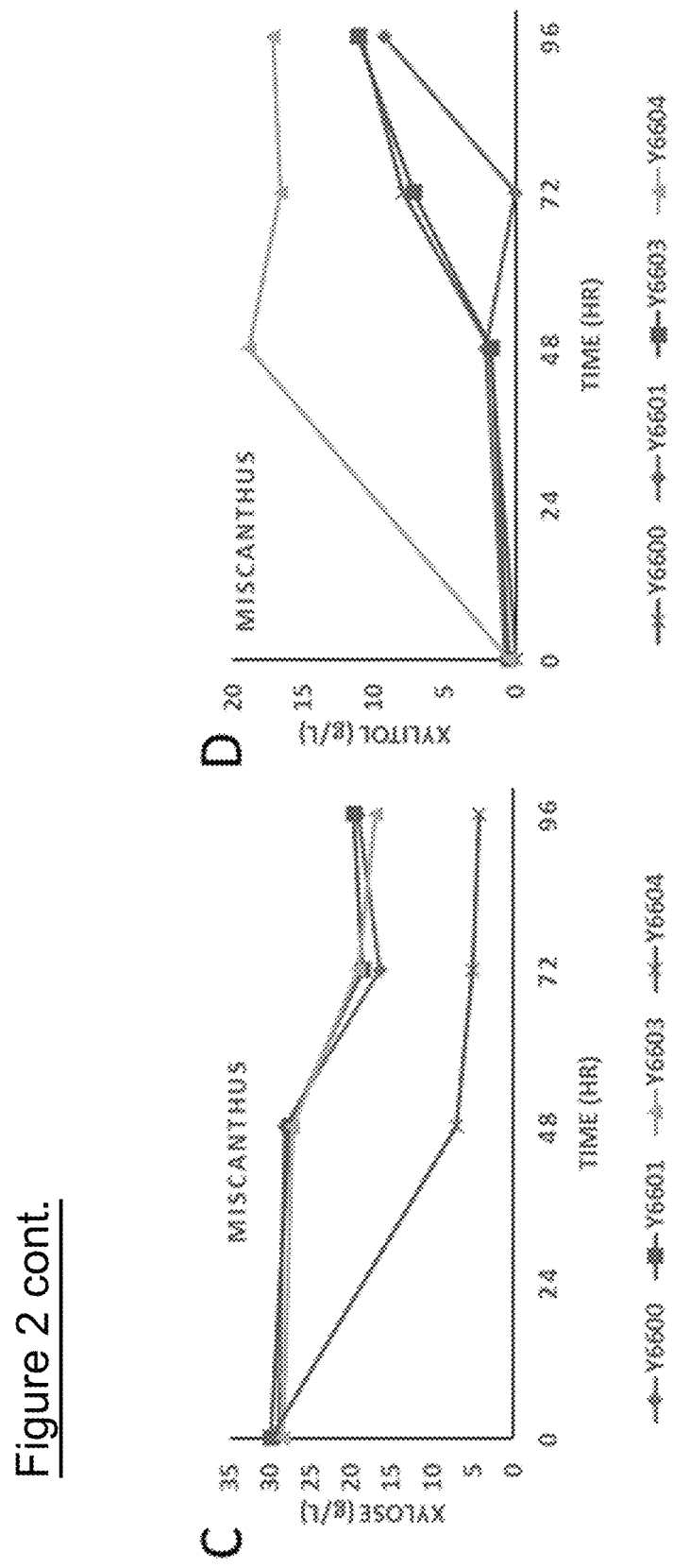
Figure 2:
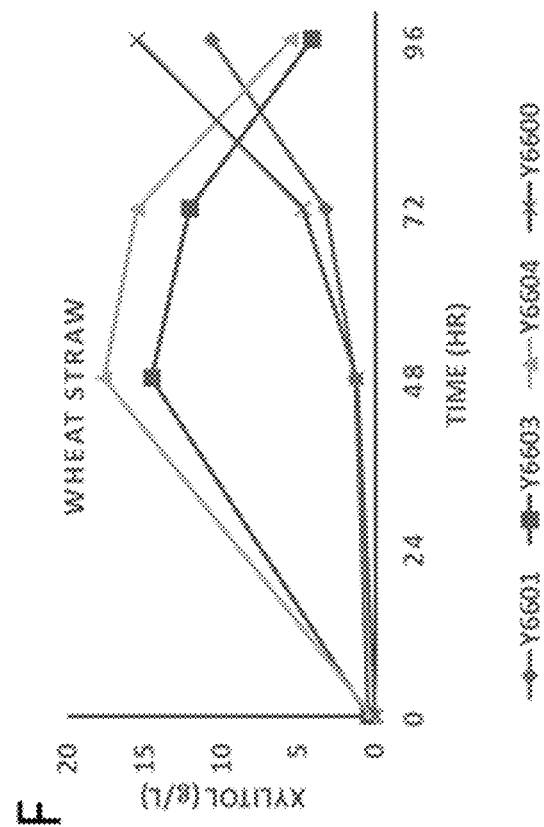
Figure 2:
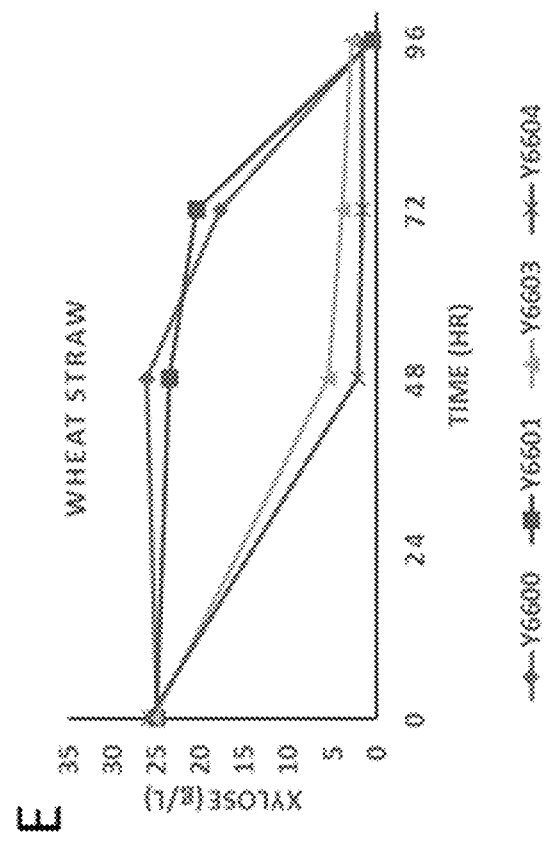
Figure 3:
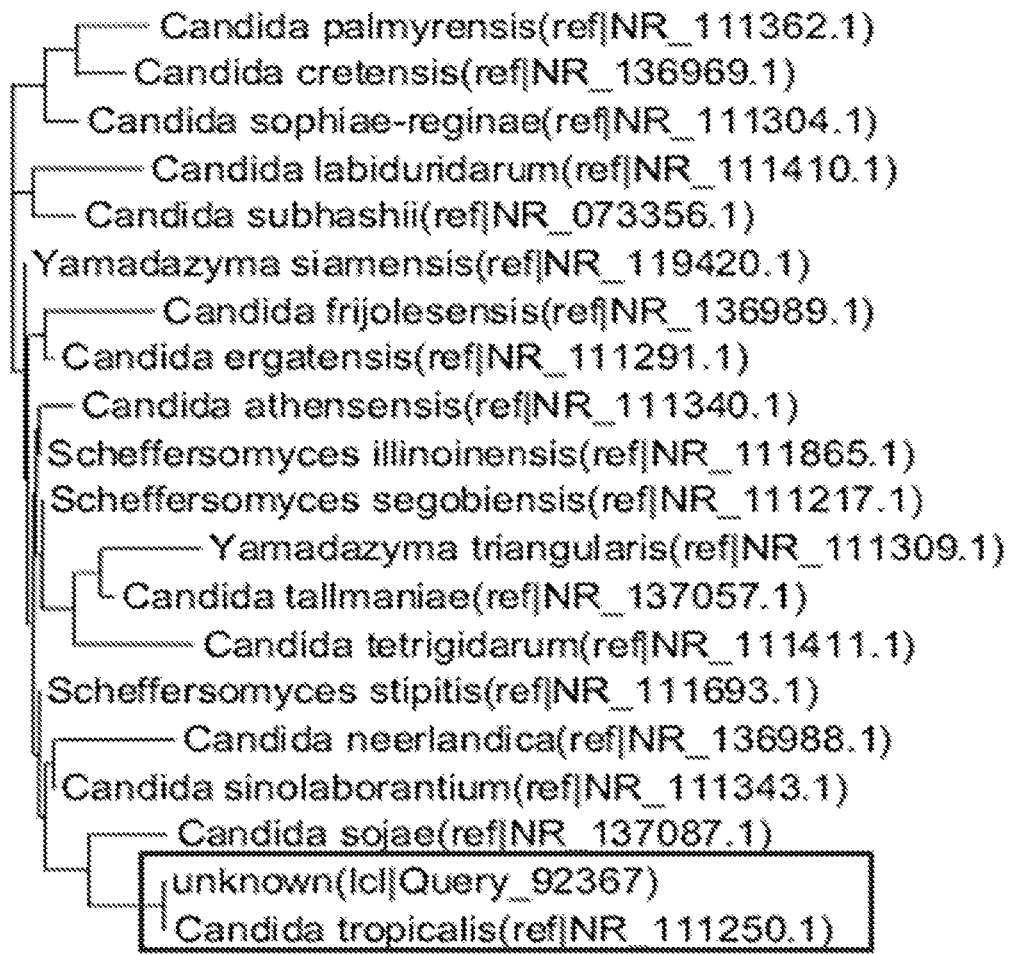
Figure 4:
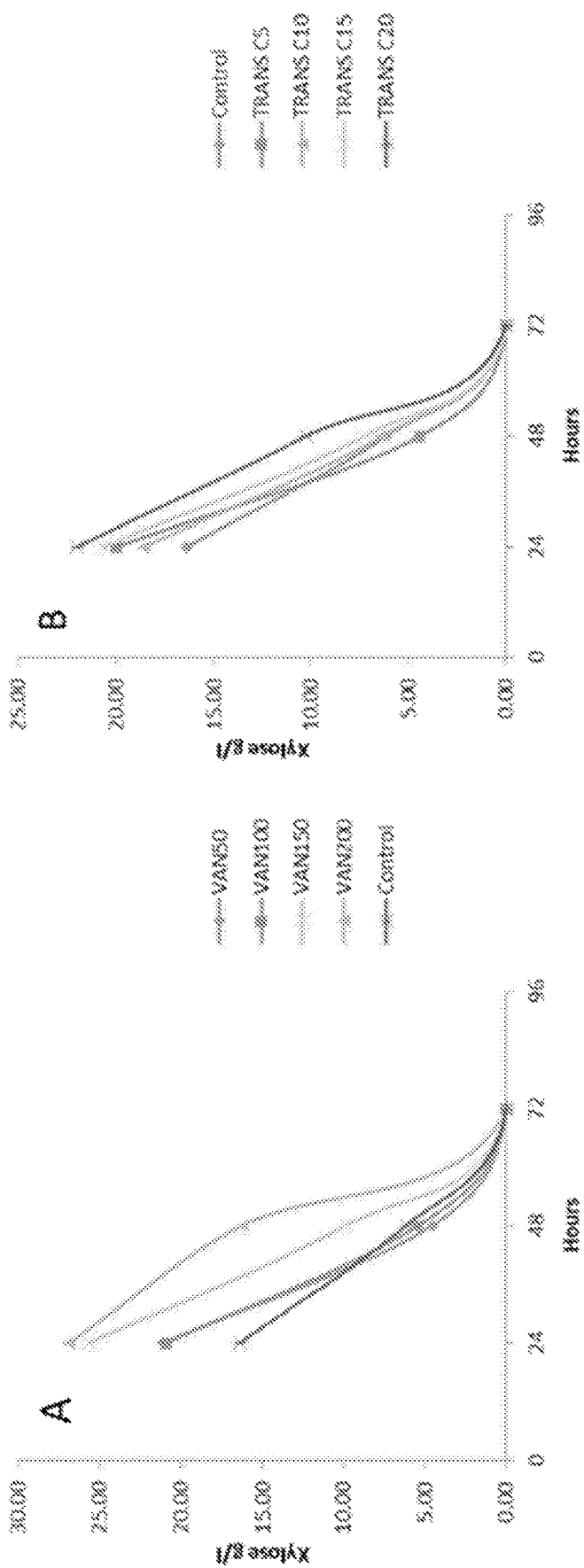
Figure 4:
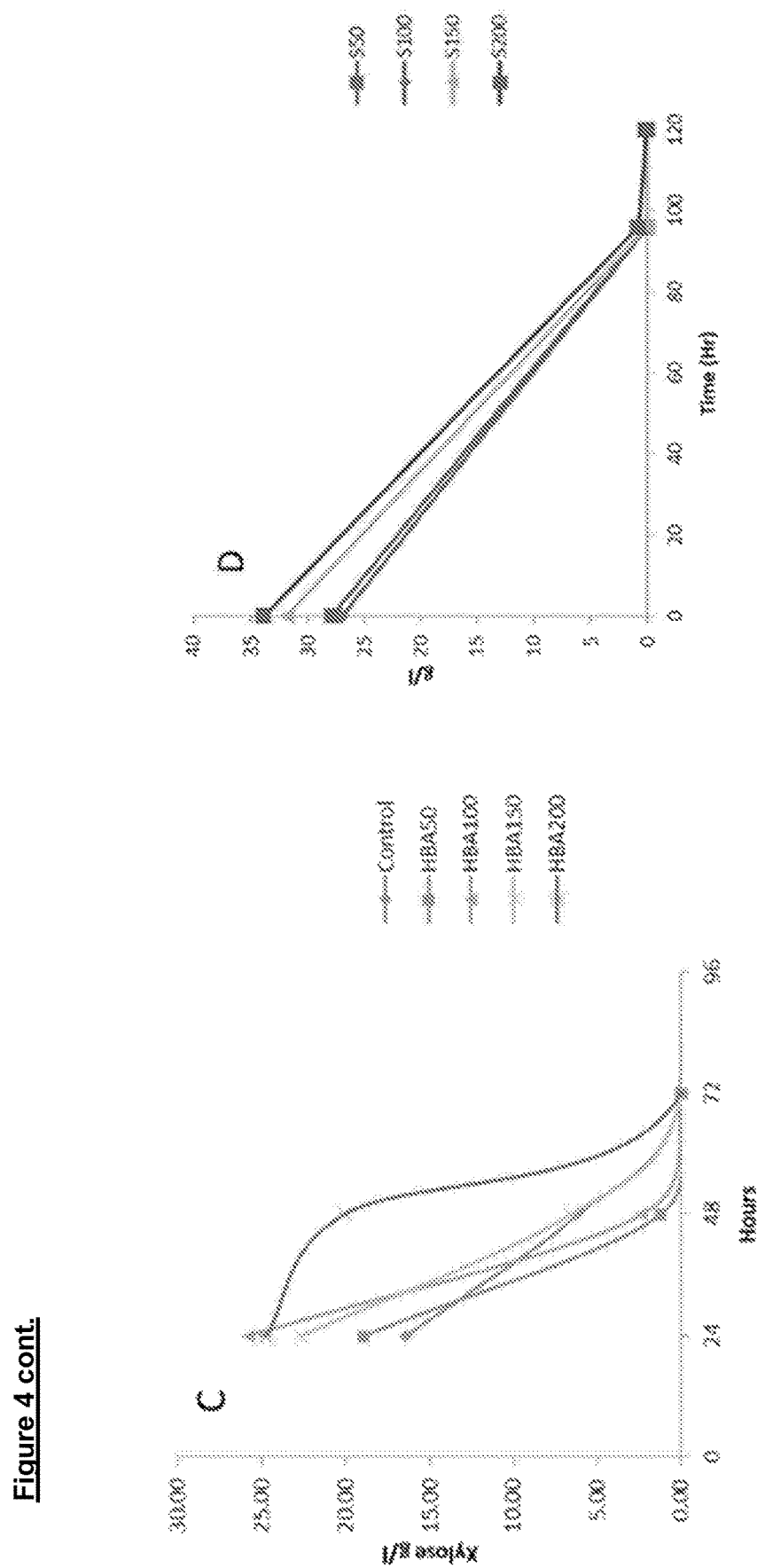
Figure 4:
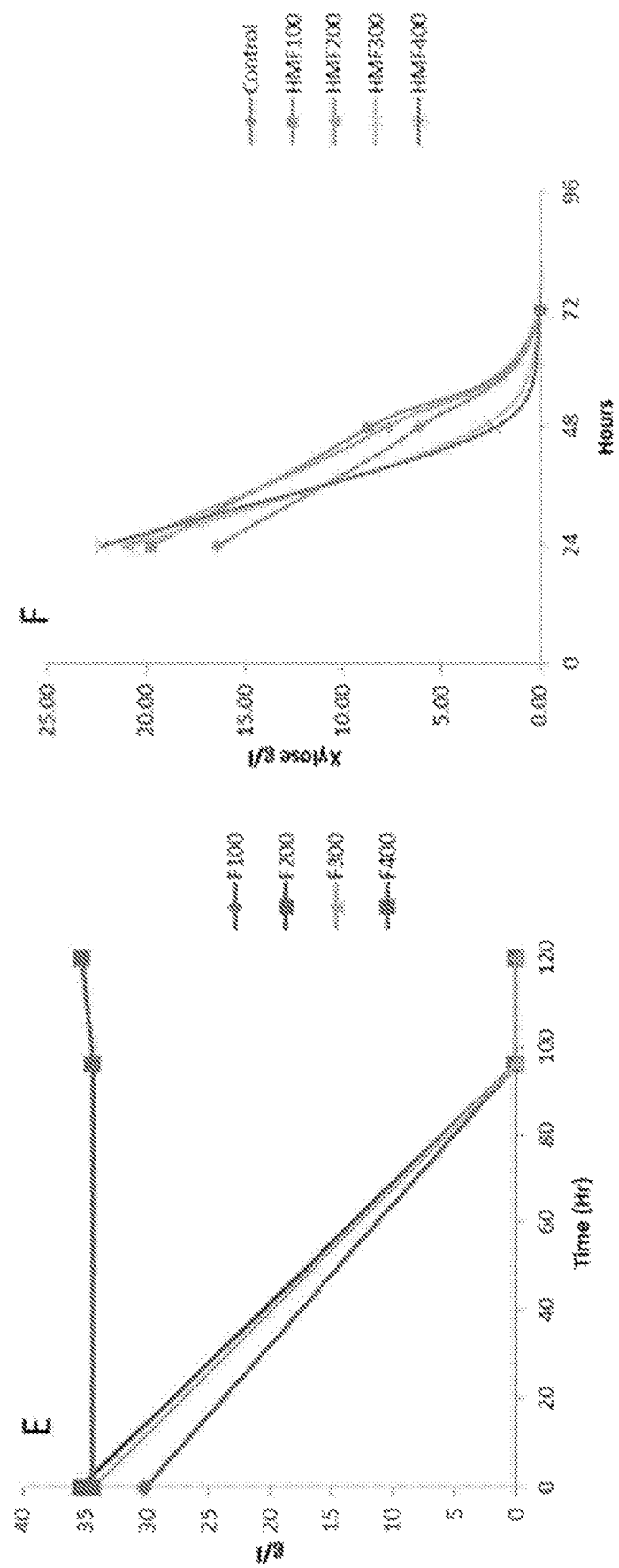

Strain Y6604 (NCYC 4190) was compared with other xylose-utilizing isolates from the gut of click beetle to assess its inhibitor tolerance and xylose to xylitol conversion. Microbial growth assessments with increasing sugar and inhibitor concentrations in mild acid hydrolysates from different feed stocks suggested enhanced growth phenotype of Y6604 (NCYC 4190) in *Miscanthus* and willow hydrolysates (FIGS. 1 A & B) whilst comparatively similar and slightly diminished growth in wheat straw (FIG. 1C) and corn stover (FIG. 1D) hydrolysates respectively. Despite slower Y6604 (NCYC 4190) growth in corn stover hydrolysate, xylose consumption and subsequent xylitol production was largely unaffected when compared to other isolates (FIG. 2 A, B) and increased amounts of the sugar alcohol at a comparatively higher rate of production were apparent in hydrolysates obtained from *Miscanthus* (FIG. 2 C, D) and wheat straw (FIG. 2 E, F). Phylogenetic analysis of the D1/D2 domain confirmed strain identity to be *Candida tropiclis* (FIG. 3). Having observed the enhanced efficacy of Y6604 (NCYC 4190) in hydrolysates with high inhibitor loadings, the isolate's tolerance threshold to common inhibitors by measuring xylose uptake rates (FIG. 4) was then assessed. Whilst high concentrations of vanillin, transcinnamic acid, hydroxyl-benzaldehyde and syringaldehyde (graphs 4A, B, C and D respectively) delayed xylose utilisation, complete attenuation of the pentose was still achieved within 72 hr. In accordance with previous reports (Wang et al. 2013), furfural was the most toxic since high concentrations completely abolished xylose uptake (FIG. 4, graph E), whereas increasing concentrations of HMF were found to enhance pentose uptake (FIG. 4, graph F). Overall, Y6604 (NCYC 4190) behaviour under synergistic toxicity of multiple inhibitors (as present in hydrolysates) or with individual inhibitors was deemed to be comparable or better than those reported in literature.

Construction of an Engineered *Candida tropicalis* Strain

Gene deletions within *Candida tropicalis* Y6604 (NCYC 4190) were achieved by using the SAT1 flipper system originally described by Reuss et al (2004) in *Candida albicans*. The primary features of the system include the presence of a *Candida* specific nourseothricin resistance marker CaSAT1 for imparting nourseothricin sensitive phenotype and maltose inducible marker recycling via a FLP recombinase under the control of a MAL2 promoter. Successful application of the SAT1 system in Y6604 required modifications to the original transformation, cellular recovery and marker recycling protocols. Transformation of Y6604 with a 5.1 kb long deletion cassette obtained via KpN1/SpH1 digestion of plasmid pΔXyl2A, yielded nourseothricin resistant colonies after 48 hr of incubation on YPD agar plates containing 200 μg/mL nourseothricin. Following cassette removal via maltose induction, PCR amplification with primers annealing to regions flanking the deletion cassette's integration site (FIG. 1B(i)) resulted in a smaller 1.3 kb long fragment in the deletion mutant than the WT (2.3 kb long fragment) indicating successful removal of one of the XYL2 alleles. Although the primers preferentially amplified the lower sized fragment, PCR with primers upstream and within the XYL2 ORF (FIG. 1B (ii)) and RT-PCR with primers within the ORF (FIG. 1C) established the presence of an intact XYL2 allele. This strain is hereinafter referred to as "ΔXyl2". Following another round of transformation (with a different gene deletion cassette obtained via double digestion of pΔXyl2B) and subsequent marker removal, both alleles were successfully removed as confirmed by both PCR and RT-PCR to yield strain ΔΔXyl2. Surprisingly, whilst the WT was able to metabolize xylose and grow on YNB-xylose plates, ΔXyl2 could not do the same (FIG. 5D) and only grew in YNB-xylose supplemented with glucose (data not shown). This is contradictory to previous reports, albeit with a different strain (Ko et al., 2006), suggesting that removal of even a single XYL2 allele can significantly compromise xylose assimilation in some *C. tropicalis* strains. Expectedly, ΔΔXYL2 was also unable to grow on YNB-xylose agar thereby establishing the strain's inability to utilize the pentose as a carbon source for microbial biomass generation. These experiments show for the first time a successful application of the SAT1 deletion system in an environmental WT *C. tropicalis* isolate. Previously reported *C. tropicalis* engineering studies for xylitol production predominantly employed lab strains with uracil autotrophy, a pre-requisite to the prominently used Ura-Blaster method. However, this requirement renders the deletion tool ineffective when modifying new isolates with no inherent nutritional predisposition.

The skilled addressee will of course appreciate that the deletion of XYL2 may be achieved by a number of methods, such as CRIPR/CAS9.

Comparing Metabolically Engineered Strains for Xylitol Production in Synthetic Media and Wheat Straw Hydrolysate FIG. 6 compares the xylose to xylitol conversion profiles of Y6604 WT (NCYC 4190), ΔXyl2 (NCYC 4185) and ΔΔXyl2 (NCYC 4186) in synthetic YEP media (graphs a, b, c). The bulk of the glucose was shown to be consumed by WT and the two deletion mutants within the first 7 hr of the fermentation suggesting no apparent impact of Xyl2 deletion upon the microbe's ability to metabolise glucose. In WT, although the rate of xylose use was sedentary until 17 hr of fermentation, rapid decline in extracellular xylose amounts was observed afterwards. Consequently, substantial xylitol accumulation occurred with an overall yield of 0.49 g xylitol/g xylose consumed ($Y_{xylose\ consumed}$) and a productivity of 0.34 g/L/h. Significantly lowered capacity of both ΔXyl2 and ΔΔXyl2 to utilize xylose in synthetic media was noticed with 71% and 87% of starting amounts respectively left unmetabolised (as opposed to 33% leftover xylose in WT). Despite the low xylose consumption, $Y_{xylose\ consumed}$ of ΔΔXyl2 was significantly higher at about 0.97 g/g which is similar to the theoretical maxima suggesting that all of the xylose consumed is getting converted into xylitol but is unable to get metabolised any further probably due to absence of XDH activity. XYL2 deletion also adversely affected cellular growth, end of fermentation $OD_{600}$ values of both mutants being roughly half of the WT. Both of the above observations i.e. lower cell growth and diminished xylose attenuation within the deletion mutants lacking xylitol flow into the pentose phosphate pathway (PPP) can be explained by compromised cellular capacity to regenerate NADPH on account of its specific requirement respectively in various anabolic reactions such as amino acid/fatty acid synthesis (Dijken and Scheffers, 1986) and in acting as a cofactor for XR mediated catalysis of the first step in xylose utilisation. Whilst glucose driven oxidative branch of the PPP has been suggested as the major contributor towards NADPH generation (Jeppson et al., 2002), its limited presence in WSH might not be enough to compensate for the role played by the proportionally higher xylose in NADPH regeneration. Supporting our previous observations on YNB-xylose agar (FIG. 1B) and in contrast to the findings of Ko et al (2006), the deletion of even a single XYL2 copy significantly compromised Y6604's xylose utilisation ability highlighting strain-specific characteristics and the essential role of XDH in xylose metabolism.

To understand the impact of XYL2 deletion upon Y4 behaviour in a complex lignocellulosic matrix, the three strains (WT and deletion mutants) were assessed for their fermentation capacity in undetoxified, acid pre-treated wheat straw hydrolysate (FIG. 6. graphs d, e, f). The starting amounts of the key sugars i.e. xylose, glucose and arabinose were not too different between the two media sets.

The WT strain was able to assimilate increased amounts of xylose in WSH when compared to the synthetic media, almost 80% of the starting xylose was attenuated by 48 hr. Final xylitol $Y_{xylose\ consumed}$ and process productivity (after 75 hr) were also enhanced at 0.73 g/g and 0.42 g xylitol/L/hr respectively. Following previous observations in synthetic media, deletion of either one or both copies of Xyl2 significantly lowered cell growth whilst increments in $Y_{xylose\ consumed}$ to 0.85 g/g and 0.98 g/g respectively were observed. Akin to the WT, both ΔXyl2 and ΔΔXyl2 demonstrated a higher xylose utilising capacity in WSH when compared to synthetic media with only 15% and 33% of initial xylose found to be unassimilated after 75 h of fermentation. One reason to explain such hydrolysate induced enhancement in strain performance could be the presence of various minor sugars that are inherently associated within hemicellulose and released in their monomeric form following steam explosion. Thus key monomeric sugars likely to be present as minor constituents of WSH, namely galactose, fructose and mannose, were quantified and have been represented together with glucose as total minor sugars (TMS). Complete utilisation of TMS was observed within 24 hr of fermentation independent of the removal of XDH activity in Y6604. It is thus likely that minor sugars act as additional substrates and their consumption aids cellular redox balance maintenance thereby resulting in enhanced xylose metabolism. Another possibility is the inhibitors playing a more direct role in enhancing the flux through the pentose utilisation pathway as observed by Wange and co-workers (Wang et al. 2015) in an unmodified *C. tropicalis* subjected to a synthetic cocktail of complex inhibitors.

Interestingly, removal of single or both XYL2 copies resulted in stepwise reduction in arabitol formation in both sets of media. In WSH, extracellular arabitol declined by 29% and 53% in ΔXYL2 and ΔΔXYL2 respectively (after 75 hr) when compared to the WT. To the best of our knowledge this is the first reported observation of declining arabitol in response to XDH inactivation in *C. tropicalis*. The overall arabitol yield ($Y_{Arabmose\ Consumed}$, $Y_{AC}$) was around 0.98 g/g in the WT and remained unaffected by XYL2 deletion. Such lack of arabitol oxidation led us to speculate that the arabinose utilisation pathway might be truncated within Y6604, although further investigations are needed to substantiate this hypothesis. In comparison to the WT, removal of one or both XYL2 paralogues enhanced the xylitol:arabitol ratio in lignocellulosic hydrolysate by 1.4 and 1.7 fold respectively (after 75 hr) and thus ΔΔXYL2 was chosen for further experimentation.

Screening Co-Substrates for Supplementation in WSH

Different compounds were screened for increasing the growth and xylose utilisation potential of ΔΔXyl2 for maximal xylitol synthesis. The additives were chosen bearing in mind their plausible availability as waste streams from different sources. Whilst glucose is the main hexose constituent within most lignocellulosic biomasses, its epimer galactose is another abundant carbohydrate monomer predominantly found in the cheese and dairy waste streams (Abreu et al. 2012). Maltose can be easily and cheaply obtained via starch rich industrial waste such as potato starch waste or brewer's spent grain. Fructose is widely available in the form of fructan rich lignocellulosic grasses whilst the abundance of crude glycerol as a byproduct from biodiesel production is well recognised. In light of the differences observed in sugar utilisation between synthetic and lignocellulosic substrates, it was deemed prudent to determine the efficacy of chosen co-substrates in both minimal media and WSH.

In YNB media containing binary mixtures of xylose and different co-substrates (as shown in FIG. 7), ΔΔXyl2 assimilated glucose rapidly in early fermentation (as shown in FIG. 7A) with consequent increment in culture's $OD_{600}$ values and a short lag phase (as shown in FIG. 7C). Glucose was followed by galactose and fructose in terms of co-substrate utilisation (as shown in FIG. 7A); the extent of galactose utilisation was lower than fructose and this was also reflected in the somewhat decreased cell growth in YNB-galactose cultures (as shown in FIG. 7C). Both glycerol and maltose were consumed in a sustained manner albeit at a comparatively lower rate. This did not seem to influence cell growth in YNB-maltose which had a shorter lag phase than YNB glycerol although end of fermentation $OD_{600}$ values were not significantly different between the two cultures. However, co-substrate utilisation or cell growth were not necessarily a direct indicator of cellular ability to metabolize xylose. Glucose addition resulted in attenuation of only 5% of starting xylose with galactose and fructose respectively aiding 34% and 54% of initial xylose's assimilation (as shown in FIG. 7E). The effect of glycerol addition on xylose consumption was similar to that of fructose, with both additives converting around 0.4 g of xylose per hr (as shown in FIG. 7E). Maltose was the most efficacious of the investigative co-substrates in aiding xylose metabolism, both in terms of the extent (bioconversion of 70% of initial xylose) and rate (0.5 g xylose per hr) of conversion of the pentose. As observed earlier with comparisons between YEP and WSH, the double Xyl2 mutant was largely more adept at both co-substrate and xylose utilisation in WSH when compared to minimal YNB media. Both glucose and fructose were ingested relatively rapidly by ΔΔXyl2 in WSH (as shown in FIG. 7B). Whilst glucose supplementation continued to stimulate cell growth (as shown in FIG. 7D) and being least beneficial for augmenting xylose metabolism (as shown in FIG. 3F), fructose breakdown did not have as much of a beneficial impact upon xylose uptake in WSH when compared to YNB (as shown in FIG. 7E). Conversely, in contrast to limited galactose breakdown in YNB media complete galactose exhaustion was observed within the first 7 hr of xylose bioconversion (as shown in FIG. 7B) with uncompromised cell growth (as shown in FIG. 7D) and subsequent conversion of more than 90% of the starting xylose (as shown in FIG. 7F). Despite the improved galactose utilisation, the rate of xylose conversion in WSH-galactose (0.5 g/hr) was lower than that observed in WSH supplemented with maltose (0.78 g/hr). Mimicking the improved xylose bioconversion by maltose addition in YNB, ΔΔXyl2 yielded the highest rate of xylose bioconversion in WSH-maltose and was able to attenuate more than 95% of starting xylose by 72 hr (as shown in FIG. 7F). Glycerol addition also led to almost complete xylose utilisation (around 94%) (as shown in FIG. 7F) and both maltose and glycerol were chosen for further analysis. Irrespective of the type of co-substrate used, $Y_{xylose\ consumed}$ was 92-96% of the theoretical maxima (data not shown).

Besides xylitol, high amount of arabitol accumulation was also observed in WSH-galactose cultures when compared to other potential co-substrates (FIG. 7G). As a result, only maltose and glycerol were chosen for further assessments.

Primary ways by which different co-substrates can impact the rate of xylose utilisation are by influencing xylose transport across the cell membrane, modulating XR activity or playing a role in NADPH regeneration. Generally in yeast, both glucose and xylose are assimilated by the HXT family of sugar transporters; xylose assimilation occurring via both facilitated diffusion and xylose-proton symport. In agreement with previous observations by (Ko et al. 2006), the rather unfavourable effect of glucose on xylose conversion is. likely due to glucose-induced catabolite repression of XR induction (Young et al. 2010) (Tamburini et al. 2010). In addition, higher affinity of the common hexose transport proteins for their native substrate can competitively inhibit xylose transport (Meinander et al. 1999) (Tamburini et al. 2010) and subsequently diminish xylose metabolism. Like glucose, fructose is also known to repress the activities of both XR and XDH in *C. tropicalis* (Tamburini et al. 2010) which would explain the comparatively reduced levels of xylose use in WSH-fructose cultures. However, fructose did not seem to inhibit xylose uptake with simultaneous consumption of both sugar moieties observed in both YNB media and WSH. Unlike *S. cerevisiae* where hexose transport is entirely reliant on the common sugar transporters encoded by the HXT gene family, certain prominent members of the CUG clade (including *C. albicans* WO-1 and *C. tropicalis* MYA3404) along with others within the sub phylum Saccharomycotina seem to have acquired an additional fructose-specific high affinity $H^+$ symporter encoded by the gene FSY1 through horizontal gene transfer events (Coelho et al. 2013). Indeed, the presence of an ORF with 100% sequence identity to FSY1 homolog in *C. tropicalis* MYA-3404 was established within Y6604 (data not shown). Cross membrane active transport of galactose, maltose and glycerol in *S. cerevisiae* is well recognised (Lages & Lucas 1997) and use of these as co-substrates did not inhibit xylose uptake by ΔΔXyl2 independent of culture media. Inefficient xylose conversion in YNB-galactose cultures is in agreement with previous findings (Ko et al. 2006) and was probably fuelled by incomplete galactose utilisation yielding comparatively lower cell biomass. However, the inverse was observed in WSH with complete utilisation of both the substrate and co-substrate. The observed discrepancies in xylose utilisation between the two media sets supplemented with galactose and fructose warrant further investigation. Nevertheless, they highlight that pentose uptake trends in minimal media with limited types of sugar moieties can be remarkably different from that prevalent in complex hydrolysates from agriculture residues. This is likely to arise from the extensive interdependence between both the cross-membrane transport and metabolism of different sugar fractions typically present in lignocellulosic hydrolysates. Following previous reports, glycerol addition in both YNB and WSH enhanced xylose conversion (Ko et al. 2006). However, in sharp contrast to previous findings, maltose was the ideal co-substrate for *C. tropicalis*, albeit a different strain, ensuring adequate biomass growth and maximal rates of xylose to xylitol bioconversion independent of the fermentation media.

Optimising the Feed Levels of Co-Substrates

Having established the efficacy of different co-substrates, the optimal levels of maltose and glycerol required by ΔΔXyl2 for xylitol synthesis was further investigated by looking at different xylose:co-substrate ratios (of 1:6, 1:3 and 1:2 represented by 0.5%, 1% and 1.5% co-substrate with 3% xylose, all w/v). Following earlier observations, maltose resulted in significantly higher growth of the deletion strain (as shown in FIG. 8A) with concomitantly increased rate of xylose consumption (as shown in FIG. 8B) when compared to glycerol. Xylose:maltose ratio of 6:1 yielded optimal attenuation of the pentose in WSH cultures and higher co-substrate amounts neither enhanced the cell growth nor the rate of xylose consumption.

Assessing the Impact of XYL2 Deletion on Arabitol Production

Following from our earlier observations of diminished arabitol synthesis in XYL2 deletion mutants (FIG. 6), we conducted further assessments to better understand the phenomenon. Y6604 WT and ΔΔXYL2 were cultured in maltose-supplemented YEP media containing similar concentrations of xylose and arabinose to provide enough carbon source for robust cell growth and avoid any ambiguities arising from differing pentose concentrations. Xylose was preferentially assimilated over arabinose with concomitant production of increased xylitol over arabitol in both strains. Deletion of XDH curtailed uptake of both xylose and arabinose, albeit to a greater extent for the latter. Whilst xylose consumption was reduced by 1.2 fold, arabinose uptake was approximately 2 fold lower. In support of our observations, over- or under-expression of XDH using promoters of varying strengths established a direct correlation between XDH activity and xylose uptake rates in *S. cerevisiae* engineered for xylose uptake. The net sugar alcohol yield for both pentoses i.e. $Y_{XC}$ and $Y_{AC}$ (g arabitol produced/g arabinose consumed) remained unchanged translating into a 1.9 fold reduction in arabitol formation in the XYL2 null mutant. The reduced arabitol production by ΔΔXYL2 is due to diminished uptake of arabinose into the cell, although it is unclear whether this stems from lower XR activity on account of XDH deletion or perhaps lower cross membrane pentose transport.

Nevertheless, the overall xylitol:arabitol ratio within the null mutant was 2.7 fold higher than the WT due to a combination of both curtailed arabitol production and higher xylitol accumulation on account of cellular inability to further oxidise xylitol. Table 3 below shows ΔΔXYL2 pentose consumption in synthetic media containing similar xylose and arabinose concentrations (values represent the mean of duplicates with less than 5% standard deviation. YXC and YAC stand for xylitol yields).

TABLE 3

| Strain Type | Time | Xylose (g/L) | Arabinose (g/L) | Arabitol (g/L) | Xylitol (g/L) | $Y_{XC}$ (g/g) | $Y_{AC}$ (g/g) | Xylitol:Arabitol |
|---|---|---|---|---|---|---|---|---|
| WT | 0 | 38.9 | 34.5 | 0.0 | 0.0 | 0.00 | 0.00 | 0.0 |
|  | 24 | 22.2 | 30.6 | 2.6 | 9.3 | 0.55 | 0.67 | 3.6 |
|  | 48 | 8.3 | 23.7 | 10.4 | 16.4 | 0.54 | 0.97 | 1.6 |
| ΔΔXYL2 | 0 | 38.9 | 34.5 | 0.0 | 0.0 | 0.00 | 0.00 | 0.0 |
|  | 24 | 25.1 | 31.0 | 2.0 | 11.8 | 0.85 | 0.57 | 5.9 |
|  | 48 | 13.2 | 28.9 | 5.6 | 23.9 | 0.93 | 1.01 | 4.2 |

Xylitol Production in Batch Cultures of ΔΔXyl2 Using Undetoxified WSH

Having established the fermentation behaviour of ΔΔXyl2 in flasks we conducted further fermentations in bioreactors for better bioprocess control (see FIG. 9). As observed earlier, bulk of the minor sugars (including glucose) were completed depleted from the fermentation broth by the first 17 hr. Complete xylose consumption was observed following 68 hr of fermentation and xylitol accumulated at a rate of 0.62 g/L/h with an overall $Y_{xylose\ start}$ of 0.87 g/g. The apparent decline in xylitol yields could perhaps be explained by the lack of xylitol secretion rather than its intracellular conversion. Like most cellular metabolites, xylitol is passively secreted across the cell membrane via diffusion and high concentrations of the sugar alcohol in the fermentation broth can thus slow down its extracellular accumulation. In support of this hypothesis, extracellular xylitol continued to build-up until 110 hr after fermentation, albeit at a marginal rate, which improved $Y_{xylose}$ start to about 0.95 g/g and in line with prior observations in shake-flask cultures. High correlation (Pearson correlation coefficient 0.99) was observed between cell growth and xylitol excretion suggesting extent and rate of ΔΔXyl2 proliferation can directly impact sugar alcohol production. Whilst marginal arabitol accumulation was evident from the middle stages of fermentation, overall levels after 68 hr comprised less than 5% (v/v) of the total sugar alcohols present in the fermentation broth.

metabolism to less toxic intermediates. Besides a global cellular response to counteract inhibitor-mediated stress (Koppram et al. 2016), a number of pentose phosphate pathway genes (Gorsich et al. 2006) have been associated with imparting furfural tolerance; higher inocula can thus aid by providing the necessary enzymes to quickly reduce toxic inhibitors and allow quick progrerssion of xylitol accumulation. Fed-batch fermentations with ΔΔXyl2 and the optimised conditions (as shown in FIG. 10B) produced 85.5 g/L of xylitol at the rate of 0.99 g/L/h, an increase in productivity of about 60%. This is one of the fastest reported values for *C. tropicalis* using lignocellulosic hydrolysate. A comparison with previous notable reports of yeast mediated xylitol production in different lignocellulosic hydrolysates has been shown in Table 5. Arabitol levels continued to be less than below 5% of the measured total sugar alcohols.

TABLE 4

Comparison of xylitol production using different lignocellulosic feedstocks.

| Yeast Strain | Lignocellulosic Feedstock | Culture Mode3 | Yield (g/g) | Productivity (g/L/h) | Reference |
|---|---|---|---|---|---|
| *Candida athensensis* SB18 | Vegetable waste | Batch | 0.81 | 0.98 | Zhang et al 2012 |
| *Candida guilliermondii* FTI20037 | Sugar cane bagasse | Batch | 0.81 | 0.6 | Arruda et al., 2011 |
| *Candida guilliermondii* FTI20037 | Rice straw | Batch | 0.84 | 0.17 | Mussato et al., 2003 |
| *Candida tropicalis* As 2.1776 | Corncob | Fed-Batch | 0.83 | 1.01 | Li et al., 2011 |
| *Candida tropicalis* JH030 | Rice Straw | Batch | 0.71 | 0.44 | Huang et al, 2011 |
| *Debaromyces hansenii* | Sugar cane bagasse | Batch | 0.82 | 0.46 | Prakash et al, 2011 |
| *Candida tropicalis* Y6604 | Wheat Straw | Batch | 0.98 | 0.82 | This Study |
| *Candida tropicalis* Y6604 | Wheat Straw | Fed-Batch | 0.97 | 1.02 | This Study |

Table 4

Enhanced Xylitol Productivity in Optimised Batch and Fed Batch ΔΔXyl2 Cultures Using Undetoxified WSH Batch and fed-batch fermentation profiles of ΔΔXyl2 with undetoxified WSH containing an increased starting inoculum and enhanced aeration have been depicted in FIG. 10. Following earlier observations in batch cultures, xylose consumption enhanced rapidly after depletion of initial glucose with concomitant xylitol accumulation (as shown in FIG. 10A). After 76 hr of fermentation, almost 61 g/L of xylitol was produced at the rate of 0.84 g/L/h and $Y_{xylose\ start}$ of about 0.98 which is very close to maximal theoretical. Whilst the optimised bioprocess conditions enhanced the productivity by about 32%, total arabitol levels continued to remain below 5% of the measured sugar alcohol mixture. Higher molecular oxygen on account of increased aeration allows quicker NADPH regeneration thus supplying the XR's cofactor requirement. Besides the sugar substrate, fungal XR has also been shown to bind and reduce HMF and furfural to detoxify and augment cell growth (Almeida et al., 2008). Thus increased XR activity on account of higher cofactor availability is likely to have dual favourability with enhancements in both xylitol production rate and fural detoxification. Higher cell densities at the start of fermentation can mitigate the toxic effects of inhibitory aldehydes in yeast (Pienkos & Zhang 2009), particularly furfural in *C. tropicalis* (Wang et al. 2013), by quick assimilation and Fermentation Scale-Up Using ΔΔXyl2 in Wheat Straw Hydrolysate FIG. 11 shows the fermentation profile of ΔΔXyl2 in 45 L of wheat straw hydrolysate. WSH with more than 6% initial xylose was fermented with ΔΔXyl2 under aerobic conditions with continuous agitation (200 rpm) and air supply (1.5 vvm). Complete xylose exhaustion was achieved following 64 hr of fermentation producing approximately 64 g/L of xylitol. Overall xylitol yield and productivity were 0.94 g/g and 1.1 g/L/h respectively. Arabitol accumulation was also observed with end of fermentation levels of around 3.9 g/L.

Figure 12:
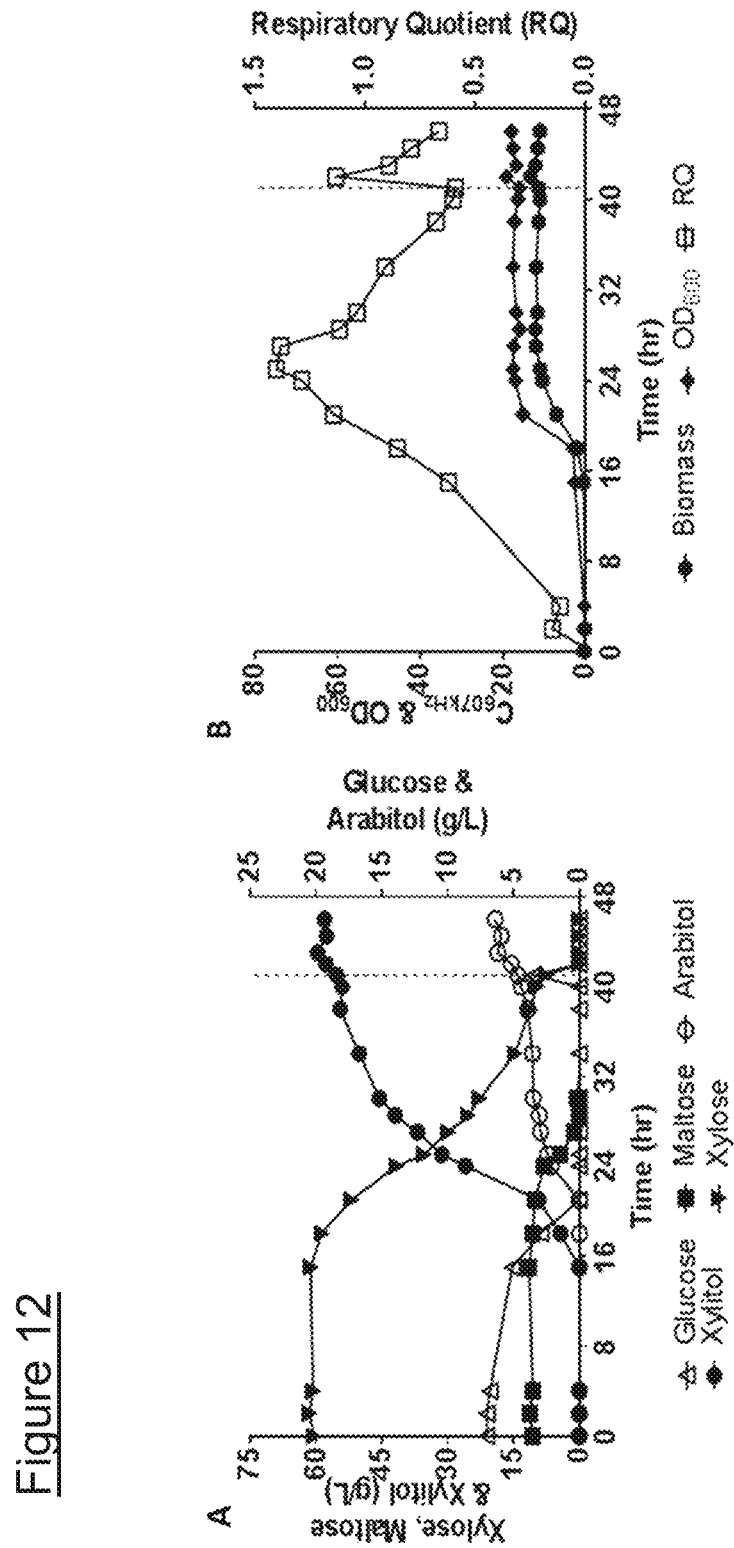

FIG. 12 demonstrates the fermentation behaviour of ΔΔXyl2 in a 140 L culture. WSH with almost 6% initial xylose was fermented under aerobic conditions (1.5 vvm) with continuous agitation (200 rpm). Remarkably, the rate of xylose utilisation was significantly faster and xylitol productivity increased by 33% to 1.6 g/L/h (until 41 hr corresponding to 87% xylose consumption) whilst high product yields were maintained ($Y_{XS}$ of 0.92 g/g) (FIG. 12A). The increased productivity can also be due to better oxygen transfer rates in the bigger reactor. The depletion of glucose and maltose was coincidental with increasing respiratory quotient (RQ) (first 27 hr of fermentation) after which a sustained decline in RQ was observed (FIG. 12B). Based on this observation, we hypothesized that lack of a carbon source for maintaining cell metabolism might be the limiting factor for achieving quicker xylitol production rates. Hence after 41 h, WSH-ΔΔXYL2 culture was spiked with a small amount of maltose (0.17% w/v) to replenish cellular carbon availability. An immediate increment in RQ was observed with complete xylose to xylitol bioconversion thereby supporting our hypothesis. Final $Y_{XS}$ and productivity for $PSF_{150-\Delta\Delta XYL}2$ were 0.96 g/g and 1.6 g/L/h respectively. Thus the use of RQ for real-time monitoring of ΔΔXYL2 performance especially when operating at industrial-scale could be highly useful. The maximal yield and high productivities achieved in this study are the highest ever reported for xylitol production using common lignocellulosic feedstocks.

Xylitol Production of Four Different Candida Strains

Figure 13:
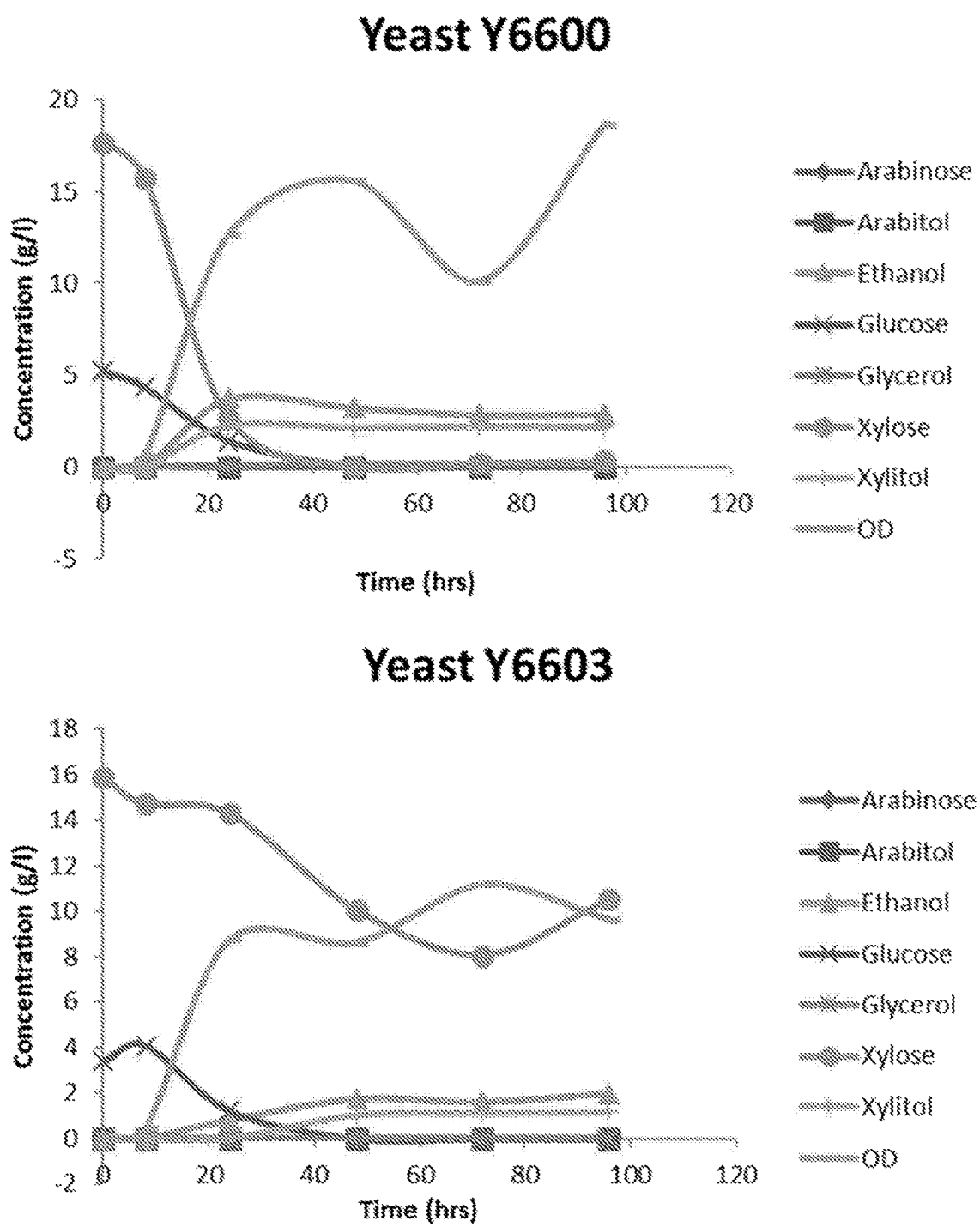
FIG. 13 shows graphs illustrating xylose to xylitol conversion of four different *Candida* strains isolated from the gut of click beetle or larvae. Values were obtained following aerobic cultivation in synthetic media supplemented with various sugars as indicated.
Figure 13:
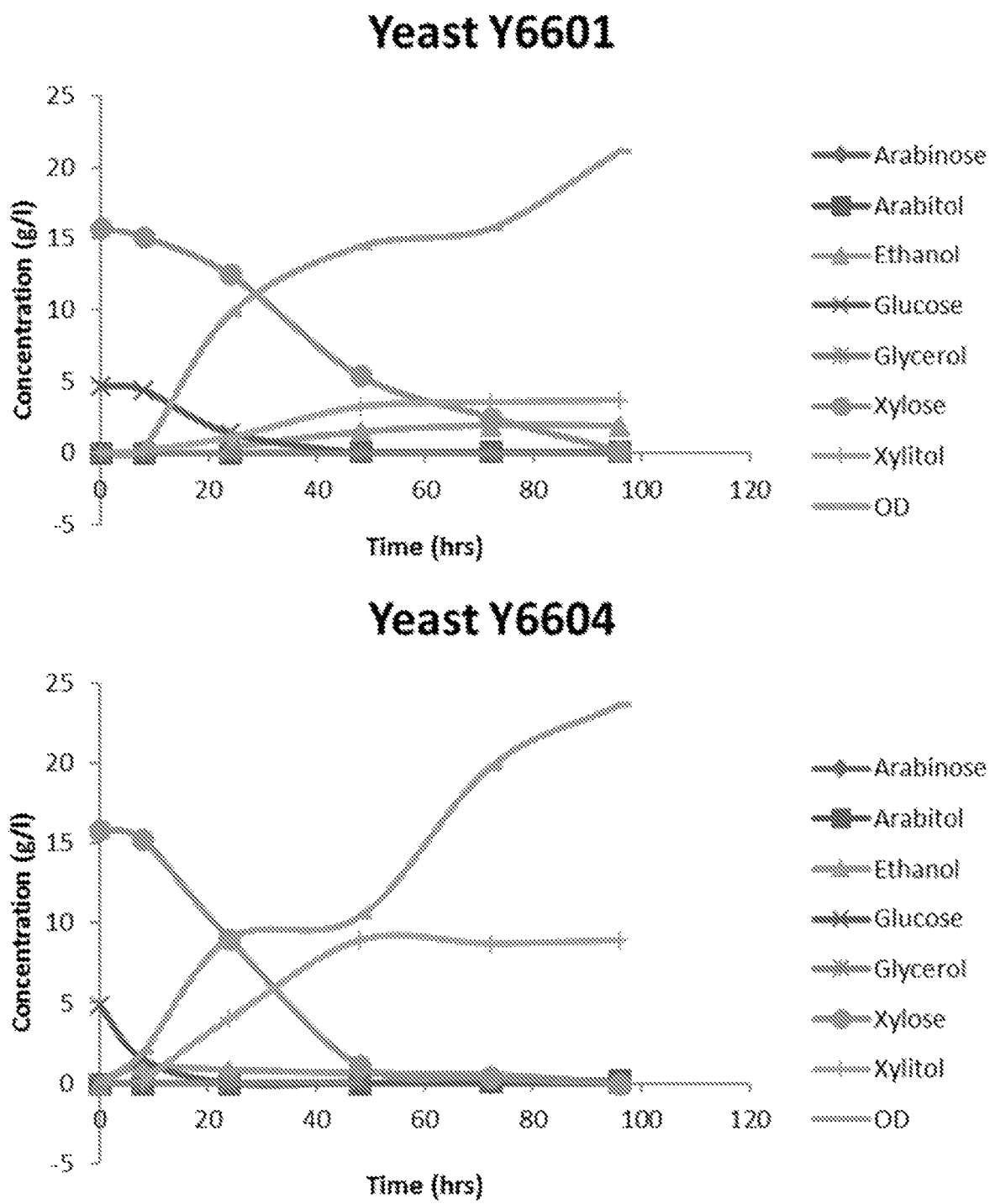
Figure 14:
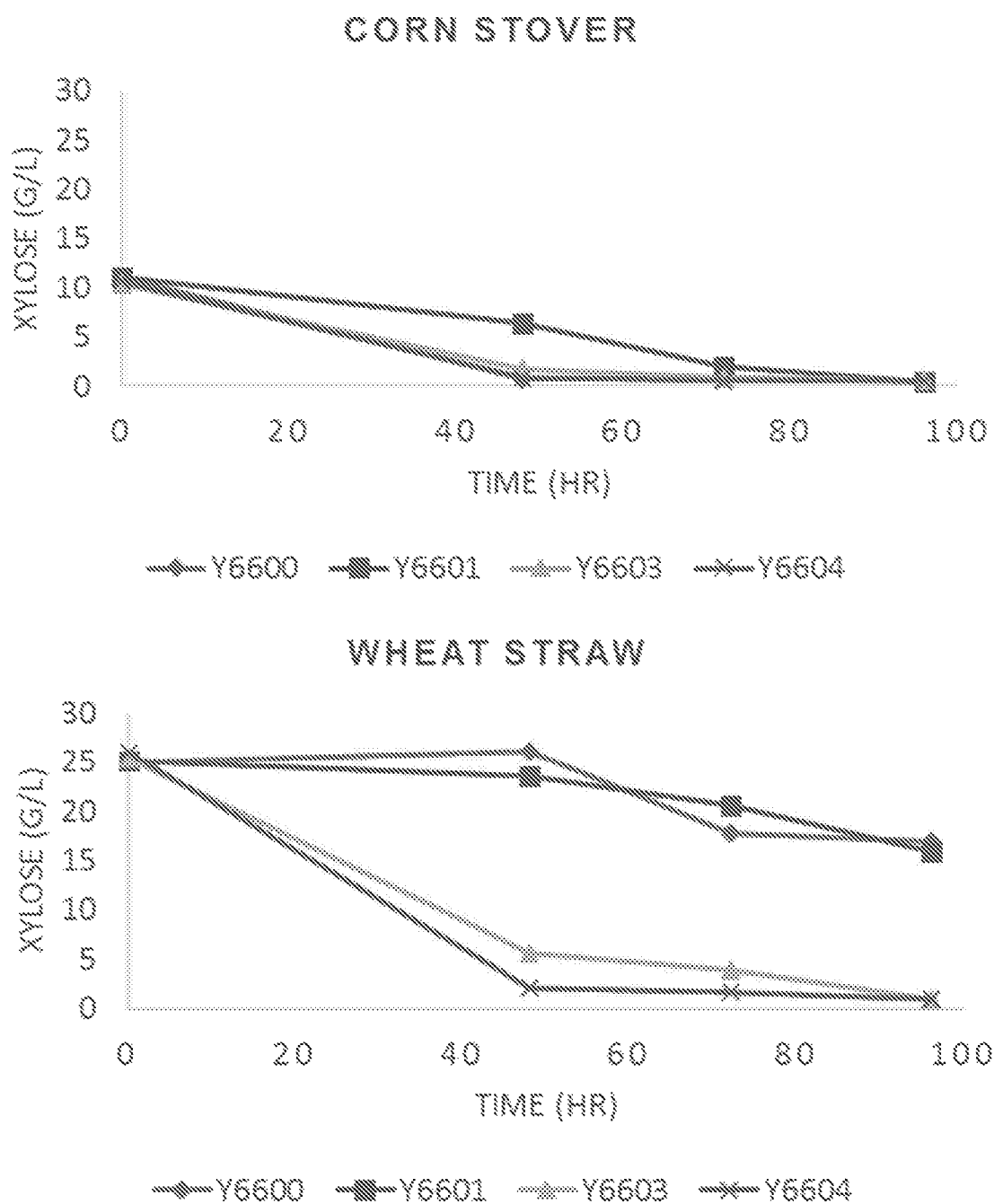
FIG. 14 shows graphs illustrating xylose utilisation by the four isolated *Candida* strains in different lignocellulosic hydrolysates. All hydrolysates were generated following steam explosion of mild acid pre-treated lignocellulosic feedstock.
Figure 14:
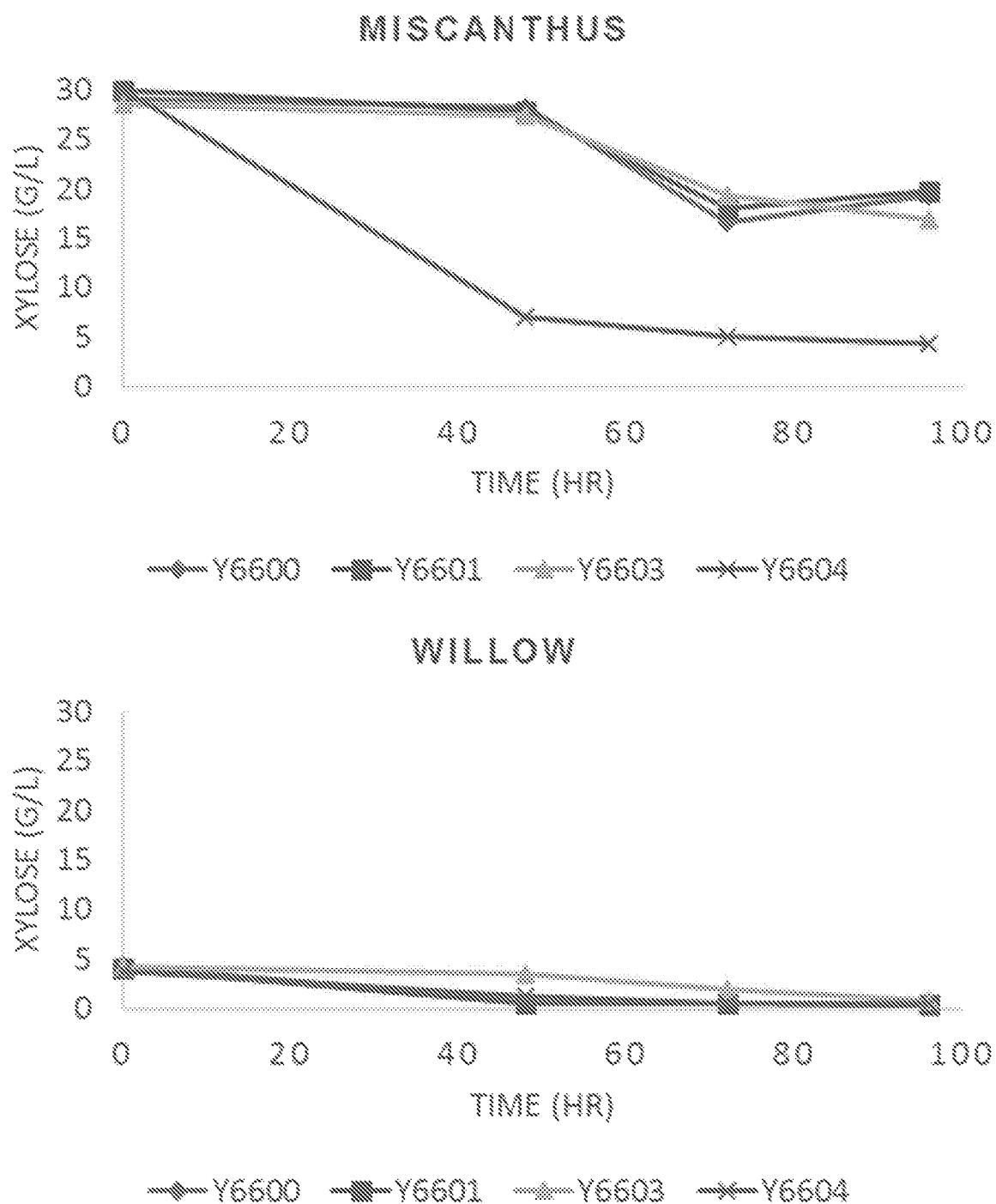

FIG. 13 shows the xylose to xylitol conversion xylitol production of different strains of four different Candida strains isolated from the gut of click beetle or larvae. The four strains isolated from the gut of click beetle or larvae were assessed for their xylose utilisation and consequently xylitol formation potential. All strains were able to consume xylose, albeit at different rates. Yeast 6600 was the quickest at consuming xylose followed by 6604 and 6601. Whilst, strain 6603 demonstrated growth on xylose it was unable to achieve complete attenuation of the pentose. Like xylose consumption, all strains were able to produce xylitol. Despite being slower than strain 6600, Y6604 demonstrated maximal xylose to xylitol conversion with highest xylitol titres of up to 6.9 g/L resulting an overall conversion yield of approximately 0.6 g xylitol/g xylose. Overall, all strains had the potential to utilize xylose and form xylitol FIG. 14 shows xylose utilisation by the four newly isolated Candida strains in different lignocellulosic hydrolysates. All hydrolysates were generated following steam explosion of mild acid pre-treated lignocellulosic feedstock. Having assessed the xylose conversion potential of the four strains in synthetic media, their efficacy at tolerating lignocellulose-derived inhibitors and utilizing the xylose present in mild acid hydrolysates were evaluated. Like in synthetic media, all new isolates were able to withstand lignocellulosic inhibitors and consume xylose across the four hydrolysates. Amongst the candidate strains, Y6604 consistently demonstrated the highest rates of xylose breakdown in the different hydrolysates with more than 75% sugar utilisation within 100 hr. Strain Y6603 matched Y6604 performance in hydrolysates derived from corn stover and wheat straw, however its xylose consumption in miscanthus and willow was much slower. Similarly, whilst strains Y6600 and Y6601 demonstrated almost complete xylose attenuation in corn stover/wheat straw and willow respectively, both were slower than Y6604 in other investigative feedstocks.

FIG. 15 shows xylitol production by the four newly isolated Candida strains in different lignocellulosic hydrolysates. In congruence with xylose uptake data, all strains were able to synthesize xylitol in the four hydrolysates. Y6604 demonstrated maximal xylitol production in wheat straw and miscanthus hydrolysates within the first 48 hr of aerobic fermentation. Following this a decline in xylitol titres was observed presumably due to the flow of the carbon into the pentose phosphate pathway and central sugar metabolism pathways on account of the action of the enzyme xylitol dehydrogenase. Final xylitol yields of the new Candida isolates in corresponding lignocellulosic hydrolysates is summarised in Table 5 below.

TABLE 5

(xylitol yields of the various Candida isolates in different lignocellusloic hydrolysates. Values represent g xylitol formed/g xylose consumed).

| Strain | Corn Stover | Miscanthus | Wheat Straw | Willow |
|---|---|---|---|---|
| 660 | 0.57 | 0.49 | 0.78 | 0.81 |
| 661 | 0.31 | 0.31 | 0.42 | 0.57 |
| 663 | 0.63 | 0.39 | 0.57 | 0.63 |
| Y4 | 0.53 | 0.63 | 0.68 | 0.48 |

For ease of reference, Table 6 below sets out the nomenclature used herein above with reference to the relevant biological deposits.

TABLE 6

| Strain Name | Other names | NCYC Accession No. | Species & Description |
|---|---|---|---|
| Y6600 | BET3 R660 | NCYC 4187 | Scheffersomyces (Candida) shehatae |
| Y6601 | BET9 R661 | NCYC 4188 | Scheffersomyces (Candida) shehatae |
| Y6603 | NW2 R663 | NCYC 4189 | Scheffersomyces (Candida) shehatae |
| Y6604 | BIO 20 R664 | NCYC 4190 | Candida tropicalis |
| Y6604 X1 | Y6604 Δχyl2 or only Δχyl2 | NCYC 4185 | Candida tropicalis Y6604 with one Xyl2 allele deleted |
| Y6604 X2 | Y6604 ΔΔχyl2 or only ΔΔχyl2 | NCYC 4186 | Candida tropicalis Y6604 with both Xyl2 alleles deleted |

Deletion of XYL2 in Strain Scheffersomyces (Candida) Shehatae Y6600 (NCYC 4187)

For deleting one copy of the XYL2 gene in NCYC 4187, a deletion cassette was assembled within plasmid pUC19 via restriction digestion cloning. A 617 bp long upstream fragment amplified using primers Y660XYL2Up-FP/-RP (Table 7 below) was digested with KpnI/XhoI whilst primers Y660XYL2Down-FP/-RP (Table 7) yielded a 619 bp long downstream fragment for subsequent digestion with SacII/SphI. The SAT1 flipper contained within plasmid pSFS2A was digested with XhoI/SacII and all three fragments were ligated in puC19 digested with KpnI/SphI to give plasmid pΔXYL2Y6600 harbouring the Y6600 specific Xyl2 deletion construct.

For Y6600 transformation, aliquots from overnight YPD cultures (10 mL) were used to inoculate 50 mL YPD in shake flasks to a representative $OD_{600}$ of 0.03-0.003 and grown overnight to $OD_{600}$ of 5.5-7.0. Harvested cell pellets were resuspended in sterile water and incubated simultaneously with TE buffer-LiAc (0.1 M, pH 8) containing DTT (10 mM) at 30° C. for 60 min. Following washes in cold water (twice) and cold sorbitol (once), 50 μL cellular suspensions were transferred into pre-cooled electroporation cuvettes, mixed with 13-15 μL of DNA (1.8-2.7 μg) and electroporated at 1.8 kV (9 kV/cm), 25 μF and 200Ω. Y6600 was recovered in 1 mL YPD for more than 5 hr at 30° C. Putative gene disruptants were selected on YPD agar containing 200 μg/mL nourseothricin after 3-4 days of incubation at 30° C.

Following Kpn1/Sph1 digestion of pΔXYL2Y6600, 2.1 ug of linear DNA was used for Y6600 transformation into Y6600. In parallel, pΔXYL2Y6600 was also used as a template for PCR-mediated deletion cassette amplification using primers Y660XYL2Up-FP/Y660XYL2Down-RP (Table 7) and similar amount of DNA was transformed into Y6600. Both sets of transformations yielded NAT-resistant (Nou') colonies, albeit a slightly higher transformation frequency was apparent when restriction digestion was employed to generate deletion cassettes as opposed to PCR (transformation frequencies restively were 4 and 1.9 Nou' colonies/μg of DNA compared). Nou' colonies were re-streaked on fresh YPD plates containing 200 μg/mL nourseothricin (FIG. 16A) and eventually screened via colony PCR. Primers binding to a region upstream of the XYL2 flanking region and within the cassette (primers Y6600Xyl2deletioncheck-FP/-RP respectively; Table 7) were used for screening in order to confirm both the presence of deletion cassette and its integration at the desired genomic locus. However despite multiple attempts no amplification could be detected in any of the Nou' colonies (lanes 1-7, FIG. 16B). This observation coupled with the fact that these colonies were able to grow in the presence of Nourseothricin (FIG. 16A) suggests that although the deletion cassette has been successfully transformed into the Y6600 genome, it seems to be undergoing non-specific homologous recombination at a different location within the genome. To further assess the legitimacy of this hypothesis, some of the Y6600 Nou' colonies were utilised for shake-flask fermentations in standard synthetic media. However, the no further conclusions could be derived (data not shown).

TABLE 7

| Primer Name | Sequence | SEQ ID |
|---|---|---|
| Y660XYL2Up-FP | ggtcggggtaccATTATTATGCGGTGGT GGTAG | 15 |
| Y660XYL2Up-RP | ggtggtctcgagGGTGAAAATGGAGGGT ATAAC | 16 |
| Y660XYL2Down-FP | ggtggtccgcggCGGTCCTGAGTAAACA ATCG | 17 |
| Y660XYL2Down-RP | ggtggtgcatgcCCTTTTGGCTGCGAAA TTTTG | 18 |
| Y6600Xyl2deletion-checkFP | CATCTATACCACCGTCAGG | 19 |
| Y6600Xyl2deletion-checkRP | GAGGACTCTGGAATTCTTATCTA | 20 |

The forgoing embodiments are not intended to limit the scope of the protection afforded by the claims, but rather to describe examples of how the invention may be put into practice.

BIOLOGICAL DEPOSITS

The application refers to the following indications of deposited biological materials:

| Name: | National Collection of Yeast Cultures |
|---|---|
| Address: | Institute of Food Research, Norwich Research Park, Norwich, Norfolk, NR4 7UA, United Kingdom. |
| Date: | 6 Jul. 2017 |
| Accession Number: | NCYC 4185 |
| Descriptor: | Candida tropicalis (Y6604 X1) |
| Depositor: | Aberystwyth University -and- |
| Date: | 6 Jul. 2017 |
| Accession Number: | NCYC 4186 |
| Descriptor: | Candida tropicalis (Y6604 X2) |
| Depositor: | Aberystwyth University -and- |
| Date: | 6 Jul. 2017 |
| Accession Number: | NCYC 4187 |
| Descriptor: | Scheffersomyces (Candida) shehatae (Y6600 (BET3 R660)) (Note: original descriptor was Candida shehatae which has subsequently been reclassified as Scheffersomyces shehatae) |
| Depositor: | Aberystwyth University -and- |
| Date: | 6 Jul. 2017 |
| Accession Number: | NCYC 4188 |
| Descriptor: | Scheffersomyces (Candida) shehatae (Y6601 (BET9 R661)) (Note: original descriptor was Candida shehatae which has subsequently been reclassified as Scheffersomyces shehatae) |
| Depositor: | Aberystwyth University -and- |
| Date: | 6 Jul. 2017 |
| Accession Number: | NCYC 4189 |
| Descriptor: | Scheffersomyces (Candida) shehatae (Y6603 (NW2 R663)) (Note: original descriptor was Candida shehatae which has subsequently been reclassified as Scheffersomyces shehatae) |
| Depositor: | Aberystwyth University -and- |
| Date: | 6 Jul. 2017 |
| Accession Number: | NCYC 4190 |
| Descriptor: | Candida tropicalis (Y6604 (BIO20 R664)) (Note: original descriptor was Candida shehatae which has subsequently been reclassified as Scheffersomyces shehatae) |
| Depositor: | Aberystwyth University |

REFERENCES

Abreu, A. P. et al., 2012. Mixotrophic cultivation of *Chlorella vulgaris* using industrial dairy waste as organic carbon source. *Bioresource Technology*, 118, pp. 61-66.

Ahmad, I. et al., 2012. Enhancement of xylitol production in *Candida tropicalis* by co-expression of two genes involved in pentose phosphate pathway. *Bioprocess and Biosystems Engineering*, 35(1-2), pp. 199-204.

Ahmad, I., Shim, W. Y. & Kim, J. H., 2013. Enhancement of xylitol production in glycerol kinase disrupted *Candida tropicalis* by co-expression of three genes involved in glycerol metabolic pathway. *Bioprocess and Biosystems Engineering*, 36(9), pp. 1279-1284.

Coelho, M. A. et al., 2013. Extensive Intra-Kingdom Horizontal Gene Transfer Converging on a Fungal Fructose Transporter Gene. *PLoS Genetics*, 9(6).

Gorsich, S. W. et al., 2006. Tolerance to furfural-induced stress is associated with pentose phosphate pathway genes ZWF1, GND1, RPE1, and TKL1 in *Saccharomyces cerevisiae*. *Applied Microbiology and Biotechnology*, 71(3), pp. 339-349.

Jeon, Y. J., Shin, H.-S. & Rogers, P. L., 2011. Xylitol production from a mutant strain of *Candida tropicalis*. *Letters in applied microbiology*, 53(1), pp. 106-13. Available at: http://www.ncbi.nlm.nih.gov/pubmed/21554342.

Jönsson, L. J., Alriksson, B. & Nilvebrant, N.-O., 2013. Bioconversion of lignocellulose: inhibitors and detoxification. *Biotechnology for biofuels*, 6(1), p. 16.

Ko, B. S. et al., 2011. Enhancement of xylitol production by attenuation of intracellular xylitol dehydrogenase activity in *Candida tropicalis*. *Biotechnology Letters*, 33(6), pp. 1209-1213.

Ko, B. S., Kim, J. & Kim, J. H., 2006. Production of xylitol from D-xylose by a xylitol dehydrogenase gene-disrupted mutant of *Candida tropicalis*. *Applied and Environmental Microbiology*, 72(6), pp. 4207-4213.

Koppram, R. et al., 2016. The presence of pretreated lignocellulosic solids from birch during *Saccharomyces cerevisiae* fermentations leads to increased tolerance to inhibitors—A proteomic study of the effects. *PLoS ONE*, 11(2).

Lages, F. & Lucas, C., 1997. Contribution to the physiological characterization of glycerol active uptake in *Saccharomyces cerevisiae*. *Biochimica et Biophysica Acta (BBA)—Bioenergetics*, 1322(1), pp. 8-18. Available at: http://linkinghub.elsevier.com/retrieve/pii/S0005272897000625.

Mäkinen, K. K. et al., 2005. Six-month polyol chewing-gum programme in kindergarten-age children: a feasibility study focusing on *mutans* streptococci and dental plaque. *International dental journal*, 55(2), pp. 81-8.

Meinander, N. Q., Boels, I. & Hahn-Hägerdal, B., 1999. Fermentation of xylose/glucose mixtures by metabolically engineered *Saccharomyces cerevisiae* strains expressing XYL1 and XYL2 from *Pichia stipitis* with and without overexpression of TAL1. *Bioresource Technology*, 68(1), pp. 79-87.

Pienkos, P. T. & Zhang, M., 2009. Role of pretreatment and conditioning processes on toxicity of lignocellulosic biomass hydrolysates. *Cellulose*, 16(4), pp. 743-762.

Porman, A. M. et al., 2013. MTL-Independent Phenotypic Switching in *Candida tropicalis* and a Dual Role for Wor1 in Regulating Switching and Filamentation. *PLoS Genetics*, 9(3).

Prasad, S., Singh, A. & Joshi, H. C., 2007. Ethanol as an alternative fuel from agricultural, industrial and urban residues. *Resources, Conservation and Recycling*, 50(1), pp. 1-39.

Reuß, O. et al., 2004. The SAT1 flipper, an optimized tool for gene disruption in *Candida albicans*. *Gene*, 341, pp. 119-127.

Sato, H. et al., 2011. The effects of oral xylitol administration on bone density in rat femur. *Odontology*, 99(1), pp. 28-33.

Seervai, R. N. H. et al., 2013. Parasexuality and ploidy change in *Candida tropicalis*. *Eukaryotic Cell*, 12(12), pp. 1629-1640.

Tamburini, E. et al., 2010. Cosubstrate effect on xylose reductase and xylitol dehydrogenase activity levels, and its consequence on xylitol production by *Candida tropicalis*. *Enzyme and Microbial Technology*, 46(5), pp. 352-359. Available at: http://dx.doi.org/10.1016/j.enzmictec.2010.01.001.

Uhari, M., Kontiokari, T. & Niemela, M., 1998. A Novel Use of Xylitol Sugar in Preventing Acute Otitis Media. *Pediatrics*, 102(4), p. 879-884.

Wang, L. et al., 2013. Effect of selected aldehydes found in the corncob hemicellulose hydrolysate on the growth and xylitol fermentation of *Candida tropicalis*. *Biotechnology Progress*, 29(5), pp. 1181-1189.

Wang, S. et al., 2015. Metabolic responses in *Candida tropicalis* to complex inhibitors during xylitol bioconversion. Fungal Genetics and Biology, 82, pp. 1-8. Available at: http://dx.doi.org/10.1016/j.fgb.2015.04.022.

Young, E., Lee, S. & Alper, H., 2010. Optimizing pentose utilization in yeast: the need for novel tools and approaches. *Biotechnology for biofuels*, 3(512), p. 24. Available at: http://www.pubmedcentral.nih.gov/articlerender.fcgi?artid=2993683&tool=pmcentrez&rendertype=abstract.

---

The invention claimed is:

1. A *Candida* strain comprising a mutation or deletion in the first XYL2 allele, second XYL2 allele, or both, wherein the *Candida* strain is *Candida tropicalis* NCYC 4185, *Candida tropicalis* NCYC 4186, *Candida tropicalis* NCYC 4190, *Scheffersomyces* (*Candida*) *shehatae* NCYC 4187, *Scheffersomyces* (*Candida*) *shehatae* NCYC 4188, or *Scheffersomyces* (*Candida*) *shehatae* NCYC 4189.

2. The *Candida* strain as claimed in claim 1, wherein the strain has been further modified so as to express an exogenous amylase.

3. A method of producing one or more sugar alcohols from a lignocellulosic feedstock, the method comprising:
    fermenting the lignocellulosic feedstock in the presence of the *Candida* strain as claimed in claim 1, under conditions sufficient to convert a sugar alcohol precursor into one or more sugar alcohols; and
    recovering the sugar alcohols;
    wherein the one or more sugar alcohols comprises xylitol.

4. The method of claim 3, wherein the one or more sugar alcohols comprises xylitol and arabitol.

5. The method as claimed in claim 4, wherein the ratio of xylitol to arabitol is greater than about 2.0 fold.

6. The method of claim 4, wherein the ratio of xylitol to arabitol is about 4:1 or more and is higher after 24 hours of fermentation time than 48 hours of fermentation time.

7. The method of claim 4, wherein the conversion of a sugar alcohol precursor into xylitol and arabitol results in a higher xylitol to arabitol ratio than strains without a mutation or deletion in the first XYL2 allele, second XYL2 allele, or both.

8. The method of claim 3, wherein maltose is present as a co-substrate during fermentation.

9. The method as claimed in claim 8, wherein glycerol is not added as a co-substrate or is only added as a minority component relative to maltose.

10. The method as claimed in claim 8, wherein the lignocellulosic feedstock comprises xylose and the xylose to maltose ratio is in the range of about 4:1 to about 8:1.

11. The method as claimed in claim 3, wherein the lignocellulosic feedstock comprises Brewers Spent Grain (BSG), wheat straw hydrolysate, or both.

12. The method as claimed in claim 11, wherein the method initially comprises the step of steam exploding mild acid impregnated wheat straw so as to form a lignocellulosic feedstock formed of undetoxified lignocellulosic hydrolysate.

13. The method as claimed in claim 3, wherein the fermentation takes place under aerobic conditions.

14. The method as claimed in claim 13, wherein the fermentation takes place under elevated aeration conditions.

15. The method as claimed in claim 3, wherein the fermentation is a batch or continuous process.

16. The method as claimed in claim 15, wherein the fermentation is a batch process which lasts up to about 70 hours.

\* \* \* \* \*